United States Patent
Quan et al.

(10) Patent No.: US 10,258,248 B2
(45) Date of Patent: *Apr. 16, 2019

(54) VECTOR-BASED SHOCK INDICATION

(71) Applicant: ZOLL Medical Corporation, Chelmsford, MA (US)

(72) Inventors: Weilun Quan, Dracut, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/868,277

(22) Filed: Jan. 11, 2018

(65) Prior Publication Data
US 2018/0220913 A1 Aug. 9, 2018

Related U.S. Application Data

(60) Continuation of application No. 15/212,371, filed on Jul. 18, 2016, now Pat. No. 9,907,477, which is a
(Continued)

(51) Int. Cl.
*A61B 5/04* (2006.01)
*A61N 1/39* (2006.01)
(Continued)

(52) U.S. Cl.
CPC ...... *A61B 5/04011* (2013.01); *A61B 5/04012* (2013.01); *A61B 5/0531* (2013.01);
(Continued)

(58) Field of Classification Search
USPC .............................................. 600/508, 510
See application file for complete search history.

(56) References Cited

U.S. PATENT DOCUMENTS

| 5,077,667 A | 12/1991 | Brown et al. |
| 5,092,341 A | 3/1992 | Kelen |

(Continued)

FOREIGN PATENT DOCUMENTS

| WO | WO 2011/100534 | 8/2011 |
| WO | WO 2012/059846 | 5/2012 |

(Continued)

OTHER PUBLICATIONS

Chaudhry, Fand A., A Novel Resuscitation Algorithm Using Waveform Analysis and End-Tidal Carbon Dioxide Pressure for Ventricular Fibrillation, University of Arizona, Biomedical Engineering Interdisciplinary Program, 2011, 39 pages.

(Continued)

*Primary Examiner* — Nicole F Lavert
(74) *Attorney, Agent, or Firm* — Fish & Richardson P.C.

(57) ABSTRACT

A system for managing care of a person receiving emergency cardiac assistance includes one or more capacitors arranged to deliver a defibrillating shock to a person; one or more electronic ports for receiving a plurality of signals from sensors for obtaining indications of an electrocardiogram (ECG) for the person; and a patient treatment module executable on one or more computer processors using code stored in non-transitory media and to provide a determination of a likelihood of success from delivering a future defibrillating shock to the person with the one or more capacitors, using a mathematical computation applied to a vector value defined by signals from at least two of the plurality of signals.

35 Claims, 11 Drawing Sheets

Related U.S. Application Data division of application No. 14/657,106, filed on Mar. 13, 2015, now Pat. No. 9,782,093.

(60) Provisional application No. 61/953,195, filed on Mar. 14, 2014.

(51) Int. Cl.
*A61B 5/00* (2006.01)
*A61B 5/053* (2006.01)
*G06F 19/00* (2018.01)

(52) U.S. Cl.
CPC .......... *A61B 5/4836* (2013.01); *A61B 5/4848* (2013.01); *A61B 5/7257* (2013.01); *A61B 5/7264* (2013.01); *A61B 5/7275* (2013.01); *A61N 1/3925* (2013.01); *A61N 1/3987* (2013.01); *A61N 1/3993* (2013.01); *G06F 19/00* (2013.01); *A61B 5/7221* (2013.01)

(56) References Cited

U.S. PATENT DOCUMENTS

| | | | |
|---|---|---|---|
| 5,741,304 | A | 4/1998 | Patwardhan et al. |
| 5,957,856 | A | 9/1999 | Weil et al. |
| 6,171,257 | B1 | 1/2001 | Weil |
| 6,224,562 | B1 | 5/2001 | Lurie et al. |
| 6,760,621 | B2 | 7/2004 | Walcott |
| 6,813,517 | B2 | 11/2004 | Daynes et al. |
| 7,269,454 | B2 | 9/2007 | Sherman |
| 7,593,772 | B2 | 9/2009 | Sherman |
| 7,774,060 | B2 | 8/2010 | Westenkow |
| 7,813,791 | B1 * | 10/2010 | Gill ..................... A61B 5/0452 600/508 |
| 7,831,299 | B2 | 11/2010 | Tan et al. |
| 7,920,917 | B2 | 4/2011 | Kelly |
| 8,165,671 | B2 | 4/2012 | Freeman et al. |
| 8,868,179 | B2 | 10/2014 | Quan et al. |
| 8,948,859 | B2 | 2/2015 | Freeman et al. |
| 9,180,304 | B2 | 11/2015 | Quan et al. |
| 9,186,521 | B2 | 11/2015 | Quan et al. |
| 9,480,853 | B2 | 11/2016 | Quan et al. |
| 9,579,515 | B2 | 2/2017 | Quan et al. |
| 9,592,402 | B2 | 3/2017 | Quan et al. |
| 9,782,093 | B2 | 10/2017 | Quan et al. |
| 9,907,477 | B2 | 3/2018 | Quan et al. |
| 2002/0026229 | A1 | 2/2002 | Weil et al. |
| 2002/0133197 | A1 | 9/2002 | Snyder et al. |
| 2002/0138106 | A1 | 9/2002 | Christini et al. |
| 2003/0055460 | A1 | 3/2003 | Owen et al. |
| 2004/0039419 | A1 | 2/2004 | Stickney et al. |
| 2004/0116969 | A1 | 6/2004 | Owen |
| 2004/0215271 | A1 | 10/2004 | Sullivan |
| 2005/0080828 | A1 | 5/2005 | Johnson |
| 2005/0245974 | A1 | 11/2005 | Sherman |
| 2005/0267536 | A1 | 12/2005 | Freeman et al. |
| 2006/0025824 | A1 | 2/2006 | Freeman |
| 2006/0116724 | A1 | 6/2006 | Synder |
| 2007/0060785 | A1 | 3/2007 | Freeman et al. |
| 2007/0100381 | A1 | 5/2007 | Snyder et al. |
| 2008/0145827 | A1 | 6/2008 | Strand et al. |
| 2008/0208070 | A1 | 8/2008 | Snyder et al. |
| 2009/0270930 | A1 | 10/2009 | Walker |
| 2009/0281413 | A1 | 11/2009 | Boyden |
| 2010/0268059 | A1 | 10/2010 | Ryu et al. |
| 2010/0298899 | A1 | 11/2010 | Donnelly et al. |
| 2011/0021938 | A1 | 1/2011 | Anderson et al. |
| 2011/0034816 | A1 | 2/2011 | Tan et al. |
| 2011/0202100 | A1 * | 8/2011 | Tan ..................... A61H 31/005 607/6 |
| 2011/0202101 | A1 | 8/2011 | Tan et al. |
| 2011/0295127 | A1 | 12/2011 | Sandler et al. |
| 2012/0010543 | A1 | 1/2012 | Johnson et al. |
| 2012/0046706 | A1 | 2/2012 | Anderson et al. |
| 2012/0191024 | A1 | 4/2012 | Halperin et al. |
| 2012/0226178 | A1 | 9/2012 | Freeman et al. |
| 2013/0138168 | A1 | 5/2013 | Quan et al. |
| 2013/0144181 | A1 | 6/2013 | Fogt et al. |
| 2013/0190634 | A1 | 7/2013 | Phillips |
| 2013/0218057 | A1 | 8/2013 | Jorgenson |
| 2014/0005738 | A1 | 1/2014 | Jorgenson et al. |
| 2014/0236030 | A1 | 8/2014 | Tan et al. |
| 2014/0277224 | A1 | 9/2014 | Quan et al. |
| 2014/0277228 | A1 | 9/2014 | Quan et al. |
| 2015/0461002 | A1 | 5/2015 | Freeman et al. |
| 2015/0257709 | A1 | 9/2015 | Quan et al. |
| 2015/0257715 | A1 | 9/2015 | Quan et al. |
| 2015/0352367 | A1 | 12/2015 | Quan et al. |
| 2015/0352369 | A1 | 12/2015 | Quan et al. |
| 2016/0023010 | A1 | 1/2016 | Quan et al. |
| 2016/0082278 | A1 | 3/2016 | Quan et al. |
| 2017/0209706 | A1 | 7/2017 | Quan et al. |

FOREIGN PATENT DOCUMENTS

| | | |
|---|---|---|
| WO | WO 2012/072518 | 6/2012 |
| WO | WO 2013/071280 | 5/2013 |

OTHER PUBLICATIONS

Chinese Office Action, CN Application 201480027256.X, dated May 30, 2016, 8 pages.
Compos et al., "An Up-Down Bayesian, Defibrillation Efficacy Estimator", Pace—Pacing and Clinical Electrophysiology, Blackwell Futura Publishing, Malden, MA, US, vol. 20, No. 5, Part 01, May 1, 1997, pp. 1292-1300.
European Search Report, 14768658.8, dated Feb. 12, 2016, 10 pages.
Extended European Search Report, PCT/US2012/065779, dated Aug. 14, 2015, 7 pages.
Extended European Search Report, European Patent Application No. 13804051.4, dated Feb. 4, 2016, 9 pages.
Huang et al, "Quantification of activation patterns during ventricular fibrillation in open-chest porcine left ventricle and septum", Heart Rhythm Elsevier, US, vol. 2, No. 7, Jul. 1, 2005, pp. 720-728.
International Search Report and Written Opinion, PCT/US2012/64779, dated Feb. 1, 2013, 8 pages.
International Search Report and Written Opinion, PCT/US2014/027431, dated Aug. 11, 2014, 14 pages.
International Search Report and Written Opinion, PCT/US2014/27514, dated Aug. 11, 2014, 8 pages.
International Search Report and Written Opinion, PCT/US2014/27658, dated Aug. 25, 2014, 19 pages.
International Search Report and Written Opinion, PCT/US2015/35174, dated Sep. 17, 2015, 13 pages.
International Search Report and Written Opinion, PCT/US2015/35189, dated Nov. 3, 2015, 20 pages.
International Search Report and Written Opinion from corresponding PCT/US2013/44750 dated Sep. 20, 2013.
Lee, Seungyup, "Mapping the Characteristics of Atrial Activation Patterns During Atrial Fibrillation," Case Western Reserve University: Department of Biomedical Engineering, Jan. 2013, 34 pages.
Povoas et al., "Predicting the success of defibrillation by electrocardiographic analysis," Resuscitation 53(1):77-82 (2002).
Watson et al., "Rapid Communication; Wavelet transform-based prediction of the likelihood of successful defibrillation for patients exhibiting ventricular fibrillation; Rapid Communication", Measurement Science and Technology, IOP, Bristol, GB, vol. 16, No. 10, Oct. 1, 2005, pp. L1-L6.
European Patent Office, Supplementary European Search Report, dated Nov. 4, 2016 for EP Application No. 14768107.6, 9 pages.
International Search Report and Written Opinion dated Jun. 10, 2016 in international application No. PCT/US2016/023992, 12 pgs.
International Preliminary Report on Patentability issued in international application No. PCT/US2016/023992, dated Sep. 26, 2017, 9 pages.
U.S. Office Action in U.S. Appl. No. 15/658,908, dated Jul. 2, 2018, 8 pages.

(56) References Cited

OTHER PUBLICATIONS

U.S. Office Action in U.S. Appl. No. 15/868,277, dated Jun. 4, 2018, 6 pages.
Wang et al., "Fourier Analysis in Polar and Spherical Coordinates," Internal Report Jan. 2008, Albert-Ludwigs University Freiburg, 2008, 26 pages.
Wang, et al., "Rotational Invariance Based on Fourier Analysis in Polar and Spherical Coordinates," IEEE Transactions on Pattern Analysis and Machine Intelligence, vol. 31, No. 9, Sep. 2009.

\* cited by examiner

VECTOR-BASED SHOCK INDICATION

CLAIM OF PRIORITY

This application is a continuation application and claims the benefit of priority under 35 USC 120 to U.S. patent application Ser. No. 15/212,371, filed on Jul. 18, 2016, which is a divisional application and claims the benefit of priority under 35 USC § 121 to U.S. patent application Ser. No. 14/657,106, filed on Mar. 13, 2015 (now U.S. Pat. No. 9,782,093), which claims priority under 35 USC § 119(e) to U.S. patent application Ser. No. 61/953,195, filed on Mar. 14, 2014. The entire contents of each application is hereby incorporated by reference.

TECHNICAL FIELD

This document relates to cardiac resuscitation systems and techniques.

BACKGROUND

Heart attacks are a common cause of death. A heart attack occurs when a portion of the heart tissue loses circulation and, as a result, becomes damaged (e.g., because of blockage in the heart vasculature). Heart attacks and other abnormalities can lead to ventricular fibrillation (VF), which is an abnormal heart rhythm (arrhythmia) that causes the heart to lose pumping capacity. If such a problem is not corrected quickly—typically within minutes—the rest of the body loses oxygen and the person dies. Therefore, prompt care of a person undergoing ventricular fibrillation can be key to a positive outcome for such a person.

One common way to treat ventricular fibrillation is through the use of an electrical defibrillator that delivers a relatively high voltage shock to the heart in order to force it back to a normal, consistent, and strong rhythm. People who have had previous problems with ventricular fibrillation may be implanted with an automatic defibrillator that constantly monitors the condition of their heart and applies a shock when necessary. Other such people may be provided with a wearable defibrillator in the form of a vest such as the LIFEVEST product from ZOLL Lifecor Corporation of Pittsburgh, Pa. Other people may be treated using an external defibrillator, such as in a hospital or via an automatic external defibrillator (AED) of the kind that is frequently seen in airports, public gymnasiums, and other public spaces. Defibrillation may be delivered in coordination with cardiopulmonary resuscitation, which centers around the provision of repeated compressions to a victim's chest, such as by a rescuer pressing downward repeatedly with the palms of the hands, or via a mechanical compression device such as the AUTOPULSE non-invasive cardiac support pump from ZOLL Medical Corporation of Chelmsford, Mass.

People undergoing ventricular fibrillation may be more receptive to a defibrillating shock in some instances compared to others. For example, research has determined that a computation of amplitude spectrum area (AMSA), or other computational methods that use either time-based or spectrum-based analytic methods on electrocardiogram (ECG) data to calculate a prediction of defibrillation shock success, may indicate whether a shock that is delivered to a person will likely result in successful defibrillation or will instead likely fail.

SUMMARY

This document describes systems and techniques that may be used to help determine when a shock on a person suffering from VF will likely be successful, i.e., will successfully defibrillate the person. By making such a determination, a medical device like a defibrillator can enable delivery of a shock only when the likelihood exceeds some threshold value (where the value is determined by professionals to have the benefit of likely defibrillation outweigh the dis-benefits of harming the patient). Alternatively, or in addition, the device can indicate to a rescuer one of a plurality of likelihood values so that the rescuer can make an informed decision about whether to deliver a shock.

The techniques discussed here receive input from a plurality of ECG leads (e.g., from a 12-lead system) and characterize that input as a vector value, where the vector that may be made up of three orthogonal (X, Y, and Z) vectors from the plurality of leads and can be understood as rotating through a complex space with each cycle of a heartbeat. A complex FFT operation may then be conducted on the vector representation in order to compute a vectorized amplitude spectrum area (AMSA) value, where the AMSA value is a numerical value that is based on the sum of the magnitude of a weighted frequency distribution from the signal, e.g., between 3 and 48 Hz. Generally, the greater the AMSA, the greater the probability that an applied shock will defibrillate the heart successfully.

Particular techniques discussed here, including selection of proper window size for the ECG data, proper window type, proper coefficients, and the use of vectorized operations in calculating the AMSA, may improve the quality of the AMSA scoring process. An AMSA score may also be used to determine where, time-wise, a person is in the process of suffering from cardiac arrest and fibrillation, since defibrillating shocks may be much less effective after a person has been fibrillating for several minutes, and CPR (including forceful CPR) may be a preferred mode of treatment instead. Such systems may also combine a current AMSA value (e.g., for recommending a shock) with a trend in AMSA value over time (e.g., for recommending chest compressions instead of a shock), where some or all of the AMSA values may be made from vectorized input.

Correlations between particular AMSA values and other inputs from sources other than an ECG (e.g., trans-thoracic impedance), on the one hand, and the likelihood that a future shock will generate a successful defibrillation, on the other hand, may be determined by analysis of historical defibrillation activity (e.g., activity collected and reported by portable defibrillators deployed in the field for hundreds or thousands actual cardiac events), and may be used to produce a mapping between observed past likelihood of success for various AMSA values and levels of prior successful defibrillations. Such data may be used, for example, to generate a look-up table or similar structure that can be loaded on other deployed or to-be-deployed defibrillators, which can be consulted in the future during other cardiac events to express a future likelihood of success that is based on the past observed success or lack of success for a corresponding AMSA value or other predictive value.

The particular parameters for computing the vectorized AMSA value may be selected so as to maximize the predictive capabilities of a medical device. For example, a tapering function may be applied to the ECG data window (e.g., by using a Tukey window), so as to improve the accuracy of the FFT applied to the data. Such a tapered window may prevent the data from jumping immediately from a zero value up the measured values, and then back down immediately to a zero value at the end of a measured window. Various parameters for the tapering function may also be applied, such as coefficients to define the slopes of the starting and ending edges of the function. Moreover, the length of the window may be selected to provide better data, such as by using a relatively short window having a duration shorter than 4 seconds, and in certain examples of about 1 second, between 1 and 2 seconds, between 1 and 3 seconds, between 2 and 3 seconds, or between 3 and 4 seconds long.

In certain other implementations, multiple different tapering functions may be applied to the same data essentially simultaneously, AMSA values may be determined from each such applied function, and the resulting AMSA value from one of the functions may be selected, or an AMSA value may be generated that is a composite from multiple different tapering functions. The window function that is used, the length of the window, and the coefficients for the window may also be adjusted dynamically, so that one or more of them change during a particular incident, or deployment, with a particular patient. For example, it may be determined from analysis of prior data that a certain window shape, size, and/or coefficients are better earlier in an episode of VF than later, so that a defibrillator may be programmed to change such parameters over the course of an event. Such changes may be tied to an initial determination about how long the patient has been in VF, which may be a function of user input (e.g., when the emergency call was made) and parameters measured by the defibrillator. Also, changes to the window type, size, and coefficients may be made from readings dynamically made from the patient under treatment. For example, AMSA values in a particular range may be measured better by a particular window type, size, or range of coefficients, so that an AMSA measurement made at time n that shows such a value, may be measured using the other parameters known to work best with that AMSA value at time n+1. Other techniques for dynamically adjusting the window type, window size, and/or coefficients may also be employed.

Upon a defibrillator making a determination of a likelihood of future success for defibrillating a patient, the defibrillator may provide an indication to a rescuer about such a determination. For example, the defibrillator may only allow a shock to be performed when the indication is sufficiently positive (e.g., over a set percentage of likelihood of success)—and may only provide a "ready for shock" light or other indication in such a situation. Also, a defibrillator may provide a display—such as a graphic that shows whether defibrillation will likely succeed (e.g., above a predetermined threshold level of likelihood of success) or provide a number (e.g., a percentage of likelihood of success) or other indication (e.g., a grade of A, B, C, D, or F) so that the rescuer can determine whether to apply a shock. In some situations, the AMSA value may serve merely to provide a recommendation to the user, with the user able to apply a shock at any time; in other situations (e.g., especially for AEDs to be used by lay rescuers), the AMSA value may be used to disable or enable the ability to deliver a shock.

The device (e.g., defibrillator) can also change the indication it presents in different situations, e.g., a dual-mode defibrillator could simply indicate whether defibrillation is advised when the defibrillator is in AED mode (and may refuse to permit delivery of a shock when it is not advised), and may provide more nuanced information when the defibrillator is in manual mode, and thus is presumably being operated by someone who can better interpret such nuanced information and act properly on it.

With respect to indications of where a victim is in the process of a VF episode—e.g., how many minutes since the victim's episode has started—an average AMSA value (including as a vectorized AMSA value) may be determined over a time period so as to identify more generalized changes in the victim's AMSA values, rather than AMSA at a particular point in time or small slice of time. For example, AMSA values can be computed for particular points in time or particular windows in time and those values can be saved (e.g., in memory of a patient monitor or defibrillator). After multiple such measurements and computations have been made, an average may be computed across multiple such values. Because AMSA generally falls (on average) over time in an episode, if the average for a certain number of readings (e.g., a moving average) falls below a particular value or falls below the value over a minimum time period (so as to indicate the general AMSA condition of the victim rather than just a transient reading), the device may provide additional feedback to a rescuer.

These general phases of cardiac arrest or VF may be identified, in one representation, as three separate phases (though there may be some overlap at the edges of the phases): electrical, circulatory, and metabolic. The electrical phase is the first several minutes of an event, and marks a period during which electric shock can be particularly effective in defibrillating the victim's heart and returning the victim to a relative satisfactory condition. The circulatory phase appears to mark a decrease in effectiveness for electric shock in defibrillating the victim, and particularly in the absence of chest compressions performed on the victim. As a result, a device such as a portable defibrillator may be programmed to stop advising shocks during such a phase (or may advise a shock only when other determinations indicate that a shock would be particularly likely to be effective) and may instead advise forceful CPR chest compressions. Such forceful compressions may maximize blood flow through the heart tissue and other parts of the body so as to extend the time that the victim may survive without lasting or substantial damage.

In the metabolic phase, chest compressions may be relatively ineffective as compared to the circulatory phase. For example, where tissue has become ischemic, such as in circulatory phase, the tissue may react favorably to the circulation of blood containing some oxygen, but where tissue has become severely ischemic, such as in the metabolic phase, the introduction of too much oxygen may be harmful to the tissue. As a result, more gentle compressions for the first period, such as 30 seconds, may need to be advised in the metabolic phase before the rescuer (or a mechanical chest compressor controlled to provide appropriate levels of compression following the points addressed here) uses a full force.

Other treatments that may be useful in the metabolic phase include extracorporeal circulation and cooling, either alone, in combination with each other, or in combination with other pharmacological treatments. In any event, observation of elapsed time since an event has begun and/or observation of the phase in which a victim is in, may be used to control a device or instruct a rescuer to switch from a first mode of providing care to a second mode of providing care in which the parameters of the provided care differ (e.g., speed or depth of chest compressions may change, temperature-based therapy may be provided or stopped, or pharmaceuticals may be administered).

In certain implementations, such systems and techniques may provide one or more advantages. For example, determinations of whether a shock should be provided or what advice to provide a rescuer based on AMSA values can be made from variables that are measured for a patient for other purposes (e.g., trans-thoracic impedance and ECG readings). The AMSA values can be improved with respective to their predictive qualities by actions such as monitoring ECG vectors and performing vectorized FFT operations to produce an AMSA value. In particular, a defibrillator may cause a rescuer to wait to provide a defibrillating shock until a time at which the shock is more likely to be effective. As a result, the patient may avoid receiving an ineffective shock, and then having to wait another cycle for another shock (which may end up being equally ineffective), and avoid the physical harm caused by any delivered shocks. And a system may guide the rescuer in providing a shock, versus providing deep chest compressions, versus providing progressive chest compressions (or may cause a device to provide such actions automatically), throughout the course of a cardiac event. Such a process may, therefore, result in the patient returning to normal cardiac function more quickly and with less stress on his or her cardiac system, which will generally lead to better patient outcomes.

In one implementation, a system for managing care of a person is disclosed and comprises one or more capacitors arranged to deliver a defibrillating shock to a patient; one or more electronic ports for receiving a plurality of signals from sensors for obtaining indications of an electrocardiogram (ECG) for the patient; and a patient treatment module executable on one or more computer processors using code stored in non-transitory media and arranged to provide a determination of a likelihood of success from delivering a future defibrillating shock to the person with the one or more capacitors, using a mathematical computation applied to a vector value defined by signals from at least two of the plurality of signals. The mathematical computation may comprise one or more vectorized Fast Fourier Transforms (FFTs), and/or one or more amplitude spectrum area calculations. The patient treatment module can be arranged to apply a pre-transform to the plurality of signals before applying the mathematical computation so as to make the plurality of signals orthogonal or near orthogonal to each other. The pre-transform can be applied in response to determining that the plurality of signals were not previously orthogonal or near orthogonal, and the patient treatment module can also be programmed to apply the mathematical computation to the vector value by calculating FFT for each of the plurality of signals to create processed values and then combine the processed values.

In some aspects, combining the processed values comprises determining a root of a sum of the processed values. Also, the mathematical computation can comprise a mathematical transform from a time domain to a frequency domain on a window of data. The window can comprise a tapered window, which may in turn comprise a Tukey window, and can be between about one second and about 2 seconds in width. The window can also be selected from a group consisting of Tukey, Hann, Blackman-Harris, and Flat Top. The system can further include an output mechanism arranged to present, to a user of the system, an indication regarding the likelihood of success from delivering a defibrillating shock with the one or more capacitors to the person. The output mechanism may comprise a visual display, and the system is programmed to display to the user one of multiple possible indications that each indicate a degree of likelihood of success, may also comprise an interlock that prevents a user from delivering a shock unless the determined likelihood of success exceeds a determined value, and may also comprise an ECG analyzer for generating an amplitude spectrum area (AMSA) value using the transform. The patient treatment module may in turn be programmed to determine whether a prior defibrillation shock was at least partially successful, and based at least in part on the determination of whether the prior defibrillation was at least partially successful, modifying a calculation of the likelihood of success from delivering the future defibrillating shock.

In yet other aspects, determining a likelihood of success from delivering a future defibrillating shock to the person depends on a determination of whether one or more prior shocks delivered to the person were successful in defibrillating the person. The mathematical transform can be selected from a group consisting of Fourier, discrete Fourier, Hilbert, discrete Hilbert, wavelet, and discrete wavelet methods. In addition, the patient treatment module can be programmed to determine the likelihood of success from delivering a future defibrillating shock using at least one patient-dependent physical parameter separate from a patient ECG reading, and can be programmed to determine the likelihood of success from delivering a future defibrillating shock using a measure of trans-thoracic impedance of the person.

In yet another implementation, a method for managing care of a person is disclosed. The method comprises monitoring, with an external defibrillator, electrocardiogram (ECG) data from a person receiving emergency cardiac assistance, the ECG data defining a vector from multiple ECG signals; performing a vectorized mathematical transform of the ECG data that defines the vector from a time domain to a frequency domain using a window in the time domain; determining a likelihood of future defibrillation shock success using at least the mathematical transformation; and affecting control of the external defibrillator based on the identification of whether a present defibrillation shock will likely be effective. The mathematical computation can comprise one or more vectorized Fast Fourier Transforms (FFTs), and one or more amplitude spectrum area (AMSA) calculations. The method can also include applying a pre-transform to the plurality of signals before applying the mathematical computation so as to make the plurality of signals orthogonal or near orthogonal, where the pre-transform can be applied in response to determining that the plurality of signals were not previously orthogonal or near orthogonal.

In some aspects, the method includes applying the mathematical computation to the vector value by calculating FFT for each of the plurality of signals to create processed values, and then combining the processed values. Also, combining the processed values can include determining a root of a sum of the processed values. The mathematical computation can also comprise a mathematical transform from a time domain to a frequency domain on a window of data, including a window of ECG data. The window can comprises a tapered window and a Tukey window, can be between about one second and about 2 seconds wide, and can be selected from a group consisting of Tukey, Hann, Blackman-Harris, and Flat Top. Also, the mathematical transform can comprise a Fast Fourier Transform.

In yet other aspects, determining a likelihood of future defibrillation shock success can comprise determining a value that is a function of electrocardiogram amplitude at particular different frequencies or frequency ranges, determining an amplitude spectrum area (AMSA) value for the ECG data, and/or adjusting the determined AMSA value using information about a prior defibrillation shock. The method can also include determining whether the adjusted AMSA value exceeds a predetermined threshold value. In addition, the method can include providing to a rescuer a visual, audible, or tactile alert that a shockable situation exists for the person receiving emergency cardiac assistance, if the adjusted AMSA value is determined to exceed the predetermined threshold value. The method can also comprise determining whether a prior defibrillation shock was at least partially successful, and based at least in part on the determination of whether the prior defibrillation was at least partially successful, modifying a calculation of the likelihood of success from delivering the future defibrillating shock.

In certain aspects, determining a likelihood of success from delivering a future defibrillating shock comprises performing a calculation by an operation selected form a group consisting of logistic regression, table look-up, neural network, and fuzzy logic, and the likelihood can be determined using at least one patient-dependent physical parameter separate from a patient ECG reading. The additional patient-dependent parameter can comprise an indication of trans-thoracic impedance of the person receiving emergency cardiac care, and the indication of trans-thoracic impedance can be determined from signals sensed by a plurality of electrocardiogram leads that also provide the EGC data. Also, under the method, the actions of monitoring, determining, identifying and affecting the control can be cyclically repeated.

In yet other aspects, the method also includes identifying compression depth of chest compressions performed on the person receiving emergency cardiac assistance, using a device on the person's sternum and in communication with the external defibrillator, and providing feedback to a rescuer performing the chest compressions, the feedback regarding rate of compression, depth of compression, or both. Also, affecting control of the defibrillator can include preventing a user from delivering a shock unless the determination of whether a shock will be effective exceeds a determined likelihood level, and displaying, to a user, an indicator of the determined indication of whether a shock will be effective. Displaying the indicator can comprise displaying a value, of multiple possible values in a range that indicates a likelihood of success.

Other features and advantages will be apparent from the description and drawings, and from the claims.

DETAILED DESCRIPTION

Figure 1A:
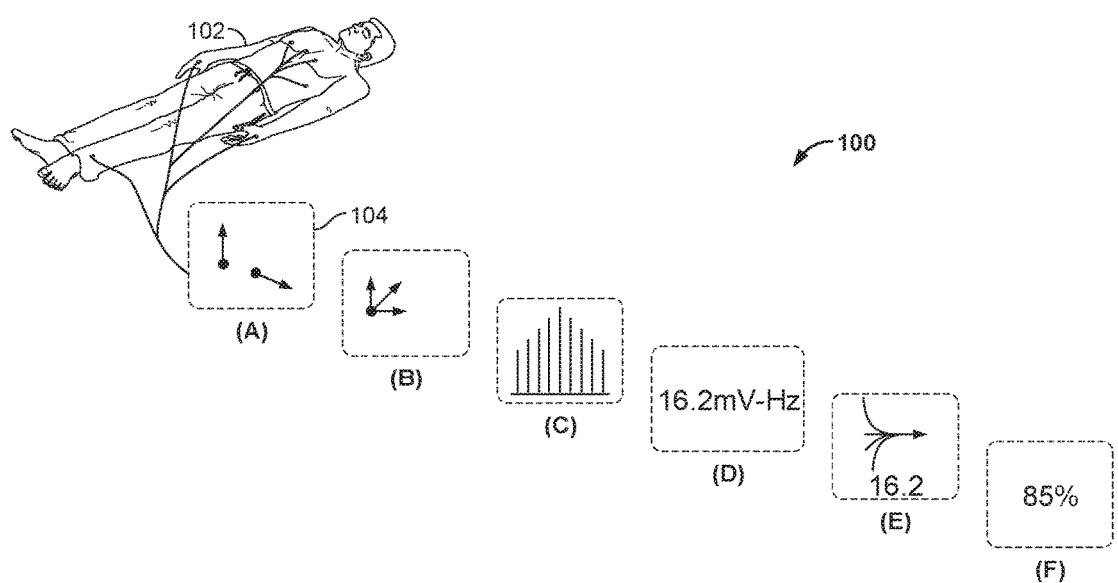
FIG. 1A is a conceptual diagram showing the use of vectorized AMSA values to determine a likelihood that a shock will successfully defibrillate a patient.

In general, defibrillation is a common treatment for various arrhythmias, such as ventricular fibrillation (VF). However, there can be undesired side effects (e.g., heart tissue damage, skin burns, etc.) that follow an electrical shock. Other undesired side effects include unnecessary interruptions of chest compressions when a shock needs to be delivered. Added to this, the effectiveness of defibrillation can fall generally over the elapsed time of a VF episode—where an episode may be measured from the time when a victim first starts feeling symptoms of cardiac arrest or loses consciousness and falls down. (Generally, the time from onset of a lethal VF episode and unconsciousness is relatively short, on the order of less than one-half minute.) It is therefore desirable to predict whether defibrillation will be successful in restoring a regular heartbeat following onset of an arrhythmic episode, and/or to determine how long it has been since a cardiac event started or what stage of the event the patient is in (e.g., a first, second, or third stage or phase).

Such predictions can each be referred to as an "indicator of success," a "success indication," or a determination and indication of a likelihood of success, within the context of the present disclosure. The prediction may cause a defibrillating shock to not be provided when the chance of successful defibrillation is low, and instead a system will wait until the chance of successful defibrillation increases to an acceptable level. Until such a time, a rescuer can be instructed to provide other care such as regular chest compressions, forceful chest compressions, or other care.

As described below, the determination of a likelihood of success can be improved by using vector values from ECG leads applied to a patient, and using vectorized FFT to make an AMSA determination. Other factors may also be considered in combination with the determined AMSA value for determining a likelihood of success, such as trans-thoracic impedance measured for a patient.

Such a determination about likelihood of successful shock can be used to alter care in an automatic and/or manual manner. In an automatic manner, a defibrillator may be made incapable of delivering a shock unless a success indication is above a determined amount. In a manual manner, the success indication may be shown to a rescuer, and the rescuer may determine whether to apply a shock or not based on the indication, or the system may provide other information to the rescuer. For example, the indication of success may show a percentage likelihood that a shock will succeed, or may be a less specific indicator, such as an indication of which phase (e.g., of three phases discussed above and below) the victim is currently in, so that the rescuer can immediately understand, from experience and training related to those phases, that defibrillation attempts are likely to be successful or not.

Additional information provided to a rescuer may take the form of instructions, such as instructions to perform chest compressions or some other action, where the action is selected from among a plurality of possible treatments based on the current phase for the victim. A system may also integrate both automatic and manual approaches—e.g., locking out the ability to provide a shock until a threshold level is reached, and then showing the relative likelihood of success above that value. The likelihood of success can be shown in various manners, such as by showing an actual percentage, or showing two or more of a low, medium, or high likelihood of success, e.g., on an electronic display of a defibrillator.

In certain implementations described herein, the present disclosure is directed to systems and methods for predicting whether defibrillation will be effective using amplitude spectrum area (AMSA) or any other appropriate Shock Prediction Algorithms (SPA) using analysis of ECG data (including in a vector format), and adjusting such SPA predictions based on either the existence of prior defibrillation shocks as well as observations of a patient's reaction to those defibrillating shocks. In particular, it has been observed that victims of cardiac fibrillation will successfully defibrillate for lower AMSA threshold values if they have been previously successfully defibrillated during the same rescue session. Thus, rather than treating each shock as a discrete event in analyzing the probability of success, the techniques described here can take into account prior shock deliveries, and an observed response of the patient to those deliveries, in determining an AMSA value or other value that will indicate that a shock currently applied to the patient will likely be successful (or not) in defibrillating the patient. Such a determination may also be combined with determinations about trans-thoracic impedance (trans-thoracic impedance) of the patient, or other measured factors, as discussed more fully below.

To obtain better predictive value for the AMSA values, the time window from which the ECG data for an AMSA determination is taken may be made relative small (e.g., between 3 and 4 seconds, between 2 and 3 seconds, and between 1 and 2 seconds), which will place the data as close to the current status of the patient as possible. Smaller windows may suffer from edge effects more-so than would larger windows, so the shape and coefficients for the windows may also be selected to maximize predictive power of the method. For example, a Tukey window having appropriate coefficients may be employed, and the measurements may be made across multiple scalar lead values with the data being processed as a vector representation of those scalar values.

FIG. 1A is a conceptual diagram showing the use of vectorized AMSA values to determine a likelihood that a shock will successfully defibrillate a patient. In the scenario 100 shown in FIG. 1A, vector values are acquired from electrodes and leads applied to the patient 102. Those values are then processed, potentially with other data, to identify a likelihood of shock success (perhaps along with other factors) and to present some indication of that likelihood to a rescuer. A series of lettered boxes shown adjacent to the patient 102 represent particular actions that a medical device, such as a portable defibrillator, make take in providing such functionality and are described in more detail below.

The patient 102 is shown as being physically connected to defibrillator 104 at box (A) by a plurality of electrode leads. Though leads may refer to individual conductors, the term will generally be used here to refer to a pair of conductors that together provide a voltage signal to the defibrillator. A typical 12-lead set-up may be used in particular implementations.

The electrodes are connected to the patient 102 so that the electrical depolarization signal generated by the beating heart arrives at different ones of the leads in a substantially orthogonal manner. In particular, the heart tissue depolarizes in a wave that defines the coordinated beat of the heart, so that electrical potential sensed by electrodes follows that order of depolarization to zones on the patient's skin that are located closest to the depolarizing zone. Thus, by placing the electrodes in appropriate locations, the phases of the relevant signals can be made near orthogonal (e.g., leading or trailing by about 90 degrees in the cycle) or out of phase (180 degrees from each other in the cycle). For example, leads may receive signals in a front-back configuration on the patient's 102 torso, or side-side, where each pair can be 90 degrees from another pair. Such placement may be achieved even for untrained users by placing the electrodes on a single sheet that might also include electrodes for shocking the patient, and that, when placed on the patient's torso, results in the sensing electrodes being at such appropriate positions. Alternatively, or in addition, graphics may be placed on the electrodes that show proper electrode placement.

The number of leads providing signals to the defibrillator 104 can vary, though two or more are generally needed in order to obtain a vectorized signal. The signals provided by two such leads are shown schematically in the box labeled (A), as multiple vectors unassociated with each other, and at box (b) as vectors represented having a common base, and each having a particular magnitude and direction at a particular point in time in a cardiac cycle. As shown, the signals from the leads are substantially, though not totally, orthogonal to each other, where a particular angle may be selected to be a zero degree point for the cardiac cycle (i.e., for each heartbeat).

At the box labeled (B), the defibrillator 104 has adjusted the signals to make them orthogonal to each by known transformation techniques to create an XYZ representation for the patient's 102 signal. For example particular signals may be projected onto orthogonal vector representations in an XYZ representation. The representation thus shows, in an orthogonal manner, the temporal change in surface potentials for the heart in a manner that is more readily susceptible to analysis and comparison to prior analysis of prior cardiac events. Use of a vector representation may permit better visibility into the condition of the heart during VF, when the heart's motion and electrical activity is not organized. For example, the analysis here may provide a better indication of the actual physical qualities of the heart during VF, as opposed to random changes that may have little or no helpful information.

In some implementations, an optimal angle for projecting the values onto an orthogonal representation can be determined. For example, a determination may first be made to identify an angle for a projection that will provide a maximum amplitude of a projection for a particular sampling interval. A maximum amplitude can then be identified in the interval from that angle. And the values may then be geometrical projected onto the coordinates of the orthogonal representation. For each sampling interval then, the process selects a configuration that provides a maximum amplitude, so that the signal is normalized from one sample to the next.

At the box labeled (C), At the box labeled (C), the Complex Discrete Fourier Transform (DFT) is applied to all components of the produced vector to transform the data from the time domain to the frequency domain. Such transform may occur in multi-dimensional space and produce data that is interpretable in a complex frequency spectrum. Such transformation may occur by standard mathematical transform methods and produce data that is interpretable in standard manners.

At the box labeled (D), the frequency domain data is used to compute an AMSA value, again by familiar mechanisms. Here, the AMSA value is 16.2 mV-Hz, though it could also be transformed to an equivalent value that is expressed in a different manner, and still be considered an AMSA value. More generally, the computation may be of a value that represents a weighted amplitude of the signal, and here generated from the signal after the FFT transformation so as to provide an indication of the signal weight in the frequency domain.

At the box labeled (E), the AMSA value is combined with other factors that are known to be "signals" that affect the success rate of defibrillating shocks applied to a patient. For example, considerations about how long the patient has been in cardiac arrest, how many prior shocks have been applied, the relative success level of those prior shocks (e.g., did they fully defibrillate or partially defibrillate, and for how long?), trans-thoracic impedance, and other possible inputs. Such values may be normalized to a common representation (e.g., some parameter-less number) and weighted according to what their respective contribution is determined to be for predicting a likelihood that a shock will be successful. Each of these input signals may be converted into a common format for all the signals (e.g., a particular dimensionless value) and as part of that process or as an additional step, each signal may be weighted so that a composite indication can be generated that properly incorporates each relevant signal at a level that such signal contributes to the likelihood that a shock will succeed or not succeed.

At the box labeled (F), the computation from such a combination (or from the AMSA or other weighted amplitude value alone) may be turned into a more human-understandable representation. As shown in the figure, that representation is expressed as a percentage likelihood of success. That number may then be displayed on a screen of the defibrillator 104 or otherwise communicated to a rescuer, such as audibly or via a screen on display on electronic glasses worn by the rescuer. The rescuer may use such information to determine the advisability of providing the shock. For example, an ambulance service may train its EMTs to only shock when the value is higher than Y early in a rescue and higher than Z later in a rescue or after unsuccessful shocks have been provided.

The likelihood may also be presented in other manners. For example, instead of or in addition to showing the percentage value, a series of red, yellow, and green colors may be displayed (e.g., from a bulb, from an icon on the screen of the defibrillator 104, or in the color of the text that shows the percentage) to represent low likelihood of success (and potential physical lock-out by the device of its ability to deliver a shock), medium likelihood of success, or high likelihood of success, respectively. Generally, the more complex representations would not be shown to lay rescuers (e.g., using AED devices) because the information could overwhelm them in an already-overwhelming situation.

In actual implementation, the received ECG-related signals will be changing constantly and cyclicly with each cycle of the beating of the patient's heart. The signals will be sampled at a particular rate (e.g., many times per second) and the likelihood calculation can be made over a window of time for each such sampling, for every nth sampling, or for multiple samplings as a group (where each reading can serve as an input to an averaging technique). A running average of the likelihood value over multiple time windows can also be maintained, and the presented indication may depend on that running average, so as to prevent large and fast fluctuations in what is displayed to the rescuer who is operating the defibrillator 104.

Figure 1B:
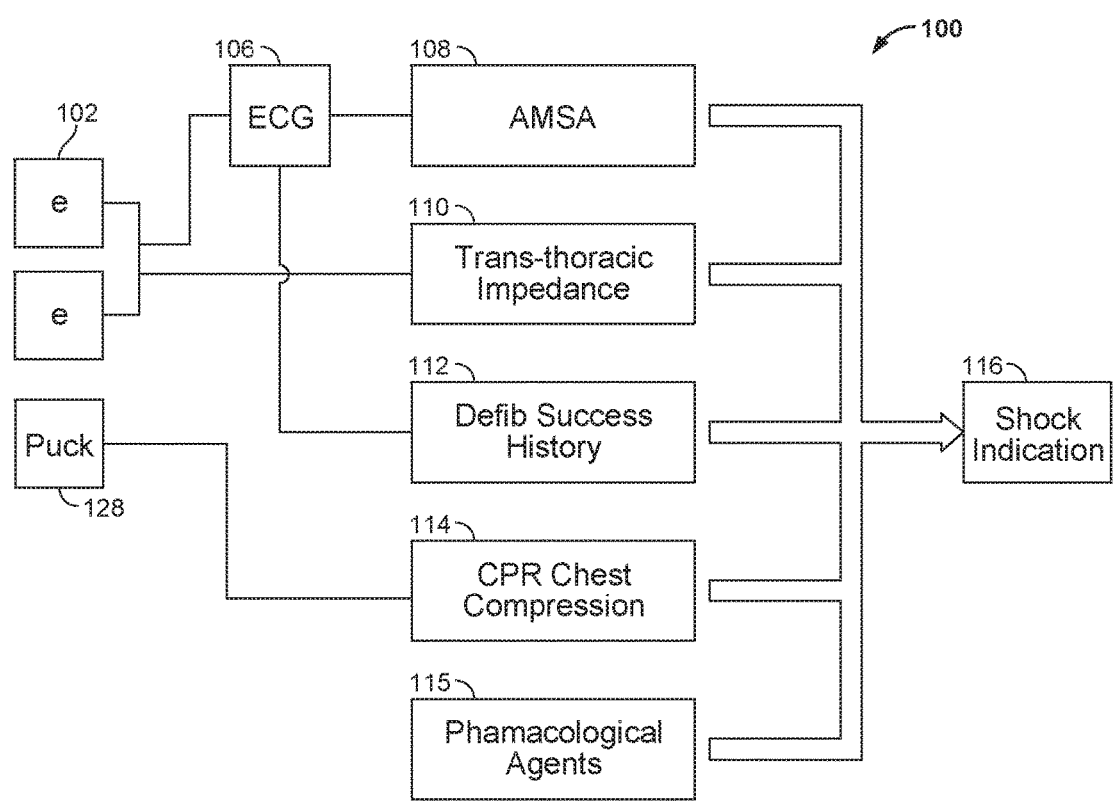
FIG. 1B shows schematically the combination of various types of data in making a determination about likely effectiveness of a defibrillating shock.

FIG. 1B shows schematically the combination of various types of data in making a determination about likely effectiveness of a defibrillating shock. In a particular implementation, one of the types of data may be used alone, or multiple of the types may be combined so as to create a composite likelihood—e.g., by giving a score to each type and a weight, and combining them all to generate a weighted composite score for a likelihood. In this example, a shock indication 116 is the outcome of a decision process that may be performed by a defibrillator alone or in combination with one or more pieces of ancillary equipment (e.g., a computing device such as a smartphone carried by a healthcare provider). The shock indication 116 can be provided to part of the defibrillator, e.g., via an analog or digital signal that represents the indication, so that the part of the defibrillator may cause a shock feature to be executed or to cause it to be enabled so that it can be manually executed by an operator of the defibrillator. The shock indication may also or alternatively be provided to the rescuer so as to indicate that the rescuer can or should cause a defibrillating shock to be delivered. (In the context of this disclosure, a defibrillating shock is one of a level designed to cause defibrillation, but it does not need to be successful in causing the defibrillation.)

The relevant inputs may obtain at least some of their data from signals generated by a pair of electrodes 103 that may be adhered to a patient's torso—above one breast and below the other, for example, in a typical manner. The electrodes may include leads for obtaining ECG data (e.g., via a 12-lead arrangement) and providing such data for analysis for a number of purposes. In addition, a CPR puck 105 may be placed on a patient's sternum and may deliver signals indicative of acceleration of the puck, and thus of up-down acceleration of the patient's sternum, which may be mathematically integrated so as to identify a depth of compression by the rescuer (and can also be used more simply to identify whether the patient is currently receiving chest compressions or not).

The electrodes 103 may be electrically connected to an ECG unit 106, which may be part of a portable defibrillator and may combine data from different leads (e.g., 8 or 12 leads) in a familiar manner to construct a signal that is representative of the patient's ECG pattern. The ECG combination may also be represented mathematically as a vector value, such as including vector components in an XYZ representation. Such an ECG signal is often used to generate a visual representation of the patient's ECG pattern on a screen of the defibrillator. The ECG-related data may also be analyzed in various ways to learn about the current condition of the patient, including in determining what sort of shock indication to provide to control the defibrillator or to display to a rescuer.

As one such example, ECG data may be provided to an AMSA analyzer 108, which may nearly continuously and repeatedly compute an AMSA number or similar indicator that represents ECG amplitude at particular different frequencies and/or frequency ranges in an aggregated form (e.g., a numeral that represents a value of the amplitude across the frequencies). Other aspects of the ECG reading may be similarly used for such analysis, and may include weighting and weighting across amplitudes of values in a range. Generally, the goal is to identify a waveform in which amplitude of the VF signals is large, and in particular, relatively large in the higher frequency ranges. Similarly, power spectrum area can be measured and its value can be used as an input that is alternative to, or in addition to, an AMSA value for purposes of making a shock indication.

As described in more detail above and below, a current AMSA value (or a combination of multiple values over a short period taken in different windows of time) can be used to determine whether a shock is likely to be successful, and a plurality of combined AMSA values, such as a running average computed many times over time (and each covering a time period longer than the time period for the first AMSA value) using a moving window may indicate how much time has elapsed since a cardiac event began and thus indicate which phase, of multiple phases during a VF event, the victim is in, where each phase calls for a different most-effective treatment sub-protocol. Also, when rescuers first arrive on a scene, several seconds of ECG data may be used to provide them an initial indication of the time since the event started and/or the phase in which the victim currently is in—e.g., by displaying a number of elapsed minutes or the name of one of multiple phases (like the three phases discussed above) on a display screen of a medical device such as a monitor or defibrillator/monitor.

The AMSA analyzer 108 may be programmed to perform the analysis of the ECG inputs, and perhaps other inputs, so as to maximize the predictive value of the AMSA readings, whether by affecting inputs to the AMSA determination, and/or making an AMSA determination and then adjusting the AMSA value that is generated from that determination. As one example, the size of the window in time from which ECG data is taken in making the calculation may be set to maximize the predictive value, such as by being about 1 second to about 1.5 seconds long. As another example, the shape of the window may be tapered, such as by being in the form of a Tukey or Hann window, rather than having vertical edges like a boxcar window. Similarly, the coefficients for the window, such as Chi2 and p may be set to maximize the expected predictive value of the calculation. The AMSA analyzer may also be programmed to change such values dynamically over the course of a particular VF incident, either by moving the values progressively as time elapses so as to make the values match known expected values for maximizing the predictive effect of the calculation, or to respond to particular readings, e.g., to use particular window length, form, or coefficients when an AMSA value is in a certain defined range.

The predictive quality of the AMSA determination may also be increased by performing the FFT or other transform in making the calculation on a vector value rather than a scalar value from the leads. Such an approach may provide a more complete picture of the operation of the heart, such as by catching minimums and maximums in the various signals more reliably and in capturing a picture of a greater portion of the heart rather than a particular point on the heart, where such point might be less representative of the overall condition of the heart. The overall process may thus better represent the actual condition of the heart, rather the non-indicative random changes in the signals.

A trans-thoracic impedance module 110 may also obtain information from sensors provided with the electrodes 103, which indicates the impedance of the patient between the locations of the two electrodes. The impedance can also be a factor in determining a shock indication as described in more detail below.

A defibrillation history success module 112 tracks the application of defibrillating shocks to the patient and whether they were successful in defibrillating the patient, and/or the level to which they were successful. For example, the module 112 may monitor the ECG waveform in time windows of various sizes for a rhythm that matches a profile of a "normal" heart rhythm, and if the normal rhythm is determined to be established for a predetermined time period after the application of a defibrillating shock, the module 112 may register the existence of a successful shock. If a shock is applied and a normal rhythm is not established within a time window after the delivery of the shock, the module 112 can register a failed shock. In addition to registering a binary value of success/fail, the module may further analyze the ECG signal to determine the level of the success or failure and may, for example, assign a score to the chance of success of each shock, such as a normalized score between 0 (no chance of success) and 1 (absolute certainty).

A CPR chest compression module 114 may receive signals about the motion of the puck 105 to determine whether chest compressions are currently being applied to the patient, and to determine the depth of such compressions. Such information may be used, for example, in giving a rescuer feedback about the pace and depth of the chest compressions (e.g., the defibrillator could generate a voice that says "push harder"). The presence of current chest compression activity may also signal the other components that a shock is not currently advisable, or that ECG data should be analyzed in a particular manner so as to remove residual artifacts in the ECG signal from the activity of the chest compressions.

Information about pharmacological agents 115 provided to a patient may also be identified and taken into account in providing a shock indication to a rescuer. Such information may be obtained manually, such as by a rescuer entering, via a screen on a defibrillator or on a tablet computer that communicates with the defibrillator, identifiers for the type of agent administered to a patient, the time of administration, and the amount administered. The information may also be obtained automatically, such as from instruments used to administer the particular pharmacological agents. The device that provides a shock indication may also take that information into account in identifying the likelihood that a shock will be successful if provided to the patient (e.g., by shifting up or down an AMSA threshold for measuring shock success likelihood), and for other relevant purposes.

One or more of the particular factors discussed here may then be fed to a shock indication module 116, which may combine them each according to an appropriate formula so as to generate a binary or analog shock indication. For example, any of the following appropriate steps may be taken: a score may be generated for each of the factors, the scores may normalized (e.g., to a 0 to 1 or 0 to 101 scale), a weighting may be applied to each of the scores to represent a determined relevance of that factor to the predictability of a shock outcome, the scores may be totaled or otherwise combined, and an indication can be determined such as a go/no go indication, a percentage of likely success, and other such indications.

In this manner then, the system 101 may take into account one or a plurality of factors in determining whether a shock to be delivered to a patient is likely to be successful. The factors may take data measured form a plurality of different inputs (e.g., ECG, trans-thoracic impedance, delivered agents, etc.), and may be combined to create a likelihood indication, such as a numerical score that is to be measured against a predetermined scale (e.g., 0 to 101% likelihood or A to F grade). Such determination may then be used to control an automatically-operated system (e.g., that delivers chest compressions mechanically), to limit operation of a manually-operated system (e.g., by enabling a shock that is triggered by a user pressing a button), or by simply providing information to a system whose shock is determined solely by a rescuer (e.g., for manual defibrillators in which the operator is a well-trained professional).

Figure 1C:
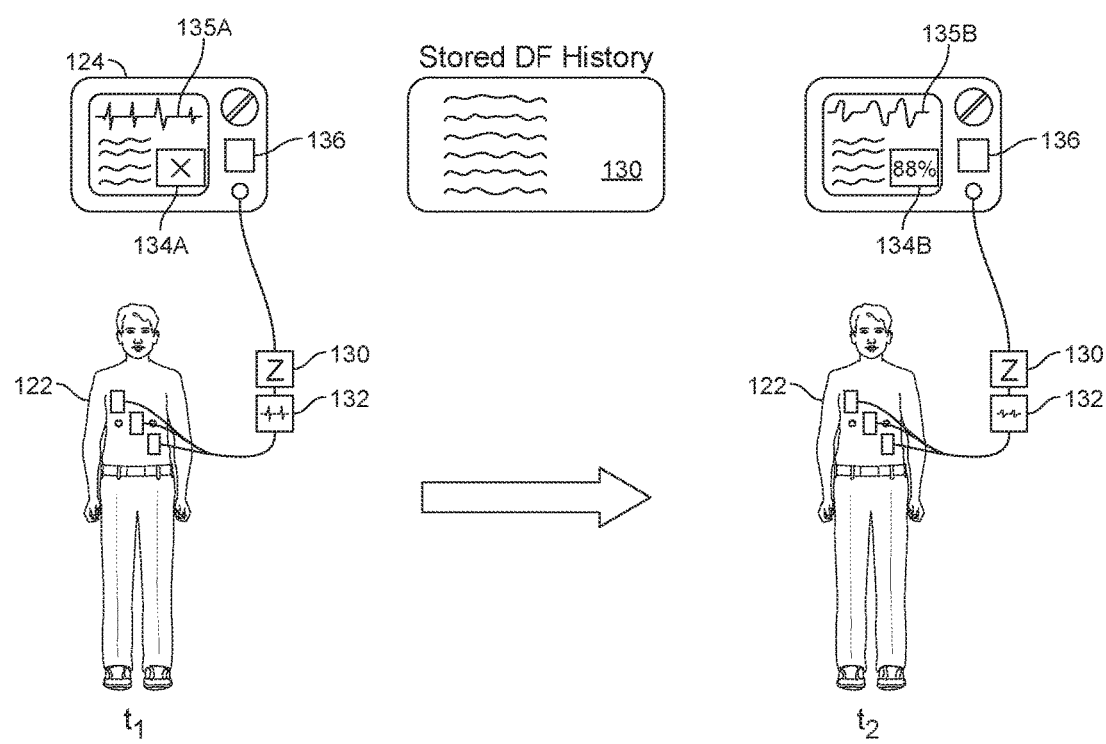
FIG. 1C shows a victim of a cardiac event being treated with a portable defibrillator.

FIG. 1C shows a victim 122 of cardiac arrest being cared for by a rescuer and a defibrillator 124. The defibrillator 124 includes an electrode package 126 and a compression puck 128 generally coupled thereto. Examples of a portable defibrillator that can be used to monitor and deliver a shock to a patient include the AED PLUS automated external defibrillator or the AED PRO automated external defibrillator, both from ZOLL Medical Corporation of Chelmsford, Mass. Other embodiments of the defibrillator 124 are possible.

In the pictured example, the victim 122 is rendered prone due to an arrhythmic episode, and the electrode package 126 and the compression puck 128 are positioned on the torso of the victim 122 in an appropriate and known arrangement. In accordance with the present disclosure, the defibrillator 124, in tandem with one or both of the electrode package 126 and the compression puck 128, is configured to determine whether a defibrillation shock will be an effective measure to terminate the arrhythmic episode. The determination is generally based on prior success or failure of defibrillating shocks, one or more trans-thoracic impedance measurements, and one or more calculated AMSA values. As shown in the figure, the victim 122 is shown at two points in time—(a) point t1 at which the patient has been defibrillated and is shown with his eyes open and a healthy ECG pattern 135A to indicate such successful defibrillation, and (b) at a later time t2, when the patient has refibrillated and is shown with closed eyes to represent such a state, and with an erratic ECG trace 135B. (Of course, there would also be a time before t1 when the patient was previously suffering from VF.)

The defibrillator 124 is configured to acquire and manipulate both a trans-thoracic impedance signal 130 and an ECG signal 132 via the electrode package. As described in further detail below, a trans-thoracic impedance measurement (Ω) is a parameter derived from the trans-thoracic impedance signal 130 that represents, among other things, thoracic fluid content. An AMSA value (V-Hz) is a parameter calculated by integrating the Fourier transform of the ECG signal 132 over a finite frequency range. The AMSA value is one form of calculation that represents a value of an ECG signal from a victim, while other SPA values may likewise be computed.

The defibrillator 124 is further configured to display an indicator 134A/B based on the defibrillating history (determined from ECG data), trans-thoracic impedance measurement(s) and AMSA value(s) obtained from the ECG signal 132, trans-thoracic impedance signal 130 and an ECG signal 132, respectively. The indicator 134A/B generally provides a perceptible cue that suggests whether or not a particular defibrillation event will likely terminate the arrhythmic episode of the victim 122. For example, for the victim 122 at time t1, the indicator 134A displays an X to indicate that no shock should be delivered to the victim 122. In contrast, at time t2, the indicator 1346 displays a success indication of "88%," so a rescuer (not shown) can be instructed "Press to Shock," so as to apply a shock to the victim 122 via actuation of a control 136 (e.g., a button that the user can actuate).

In this situation, the indication of an 88% likelihood of success was made by consulting data structure 130, which may be stored in memory of defibrillator 124 upon analysis that occurred around the time of t1, and applying an appropriate calculation to data from the data structure 130. In particular, the defibrillator may analyze ECG data and an indicator provided by shock delivery circuitry in order to determine that a shock was delivered, and at a time soon after, the patient's heart rhythm entered a normal pattern, such that the defibrillator 124 may determine that the shock was a success at time t1. Upon making such a determination, the defibrillator may update data structure 130 to indicate that a successful defibrillation event has occurred during the rescue attempt. Other shocks may also be delivered, and the data structure 130 may be updated to reflect such events, and the success or failure of such events.

Also, the ECG signal 132 may be made up of multiple separate signals taken by different ones of the leads applied to the victim 122. Such multiple signals may be used to construct one or more vectorized signals from the victim 122. The computations performed on those signals (e.g., FFT transforms) may also be performed in vectorized form so as to produce an AMSA or similar value, in manners like those discussed above and below.

Data structure 130 or another data structure may also store information about prior AMSA readings for the victim during the particular VF episode. For example, a separate AMSA measurement and calculation may be made periodically (e.g., multiple times each second, once each second, or once every several seconds) and at least some past calculated AMSA values may be stored in data structure 130. Such values may be combined, and determinations may be made about general values (with low variability because of the combining) and trends in AMSA values, where such determination may indicate information such as the progress of the victim through phases that are generally indicative of the likelihood of success of particular actions taken on the victim by a rescuer. Moreover, such information may be used to generate an indication to a rescuer of the elapsed time (approximate) since the victim entered VF, or an indication of the phase the victim is currently in, among other things.

Embodiments other than those that display a percentage likelihood for a shock indication are possible for the one likelihood indication discussed here. For example, it will be appreciated that a success indication may be implemented as any appropriate type of perceptible feedback (e.g., haptic, audio, etc.) as desired. Two simultaneous indications may also be provided, where both may be the same style of indication (e.g., visual display) or different types (e.g., visual display for one and haptic for the other)—e.g., the phase in which a victim is currently located may be displayed on a screen of a defibrillator, while a current AMSA value indicating a relatively high chance of success may be communicated by vibration of or display on a puck on which the rescuer has placed his hands (so as to encourage the rescuer to back-off and provide the shock).

In certain implementations, the defibrillator 124 may make the determination of a likelihood of success without expressly notifying the rescuer, and may simply use the determination to determine when to tell the rescuer that a shock may be delivered, or to provide other instructions to a rescuer. In other situations, the defibrillator 124 may explicitly indicate the likelihood of success, such as by showing a percentage likelihood, by showing less discrete gradiations for success (e.g., poor, good, very good, and excellent), or by displaying a range of colors (e.g., with red indicating a poor chance and green indicating a good chance). The type of indication that is displayed may also differ based on a mode in which the defibrillator 124 is operating—for example, in a professional mode, more detailed information may be provided, whereas in an AED mode, simpler information (a "go"/"no go" choice) may be presented.

In such manner then, the defibrillator may conduct a number of relatively complex calculations and may combine multiple factors in determining whether to allow a shock to be provided to a patient, or to encourage the application of such a shock by a rescuer.

Figure 1D:
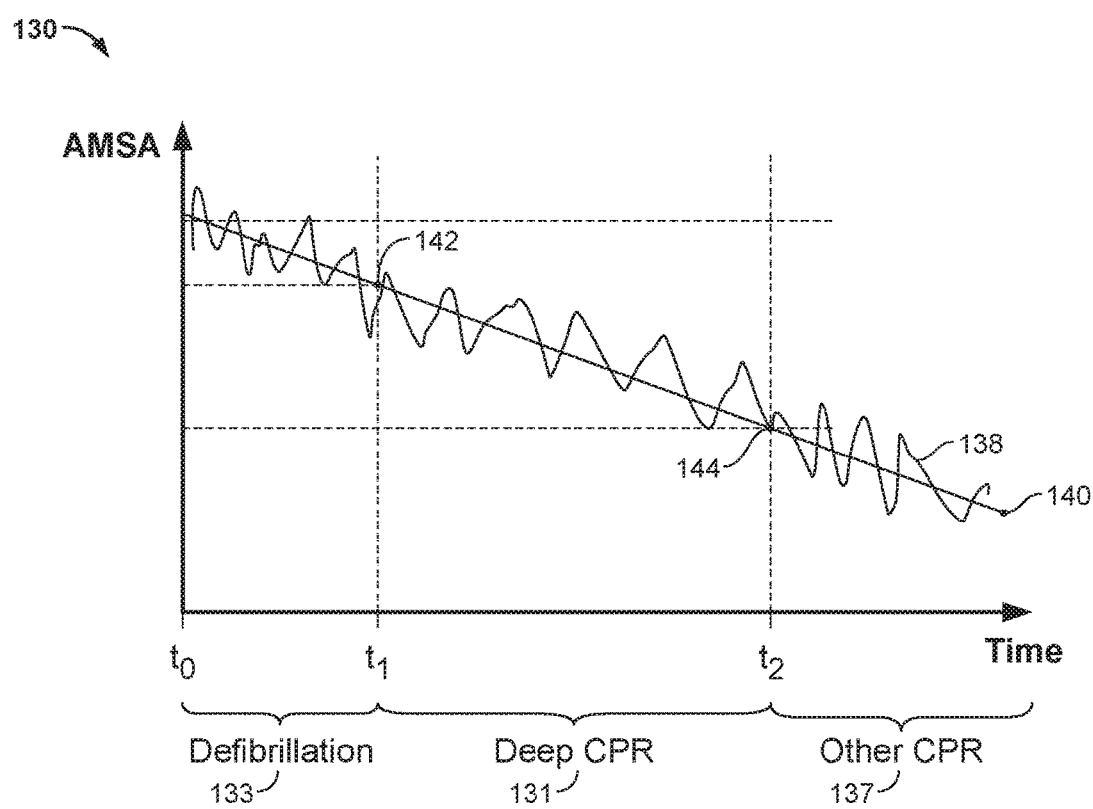
FIG. 1D is a graph that represents changes in AMSA during an event correlated to phases in the event.

FIG. 1D is a graph 130 that represents changes in AMSA during a VF event correlated to phases in the event. In general, the graph 130 shows how AMSA varies along with variations in a patient ECG, and varies more generally over a longer time period by falling over time after the event has started. Such AMSA values may be computed from vectorized ECG data in the manners described above.

The time across this graph may be, for example, about 15 minutes. The time is broken into three phases. A defibrillation phase 132 may represent about the first 4 minutes (plus or minus one minute) of the event. A deep CPR phase 131 may run from about four minutes to about 10 minutes after onset of the event. And an Other CPR phase 137 may represent the remainder of the event, assuming the victim has not been revived by that time. Each of these time periods corresponds to a particular phase in the patient's condition that may in turn correspond to a different manner in which the patient should best be treated by a rescuer Line 138 is represented as being drawn through all of the AMSA values computed periodically throughout the time of the event. (The line is shown falling linearly here for clarity, though AMSA generally decreases exponentially. If AMSA were graphed for a rescuer, it could be shown as an exponential curve, as a line on an exponential scale, and/or with error bars showing statistical variation in the readings.) As can be seen, the AMSA values vary up and down (with a general downward trend over time), and such variation represents changes in the victim's ECG where the changes can represent changes in likelihood that a shock, currently delivered, will be successful. But although there is relatively large variation over short time periods, the variation is less over longer time windows, such as over 10 or more seconds. Thus, for example, AMSA values may be computed periodically over a short time period, and more general values may be computed by averaging or otherwise combining the individual measurements. A running average is represented by line 140. Line 140 may simply represent the average of past computations, and may also be extended into the future in certain implementations, such as by linear regression or other appropriate statistical techniques. For purposes of clarity, the overall AMSA value is shown here as falling linearly with time, though the actual variation may differ from what is shown here.

In this example, two points on line 140 are particularly relevant, points 142 and 144. These points represent locations at which the combined AMSA value measurement (e.g., averaged over a window of time) fall below a predetermined value. For example, the value for point 142 may have been selected from observations of ECG data, and corresponding AMSA values from data captured for actual real-world resuscitation events with real victims, and such data may indicate that resuscitation from shock falls below an acceptable value and/or falls off more quickly upon passing below a particular AMSA value. Such AMSA value may be selected as a cut-off point that defines the line between the first phase and the second phase. Similarly, such data may indicate that chest compressions or a particular type of chest compressions, such as forceful chest compressions, fell below a particular level of effectiveness or changed relatively rapidly in their effectiveness past another AMSA value. As such, point 144 may represent an AMSA value determined from such data analysis to correspond to such changes as observed across the large population of VF events. The points 142, 144 are mapped to the determined values with horizontal dotted lines, and a defibrillator or other device may monitor the combined AMSA value as an event progresses so as to identify when the predetermined AMSA value is reached. A similar monitoring may be employed with respect to identifying the existence of point 144.

Each of the points 142, 144 is also mapped to the time axis, representing the time at which the particular victim was determined to have transitioned from one phase to another. Generally, the times will be relatively similar as between different victims and different cardiac events, where the changes are driven in large part by ischemic effects that the event has on the heart tissue. At such points in time for the particular victim represented by this graph, the behavior of a medical device such as a defibrillator that is treating the victim may change in the ways discussed above and below.

As such, the device may determine an estimated time since the VF event began using AMSA values and/or other information, where particular AMSA values from a studied population have been determined to correspond to certain times since collapse or other instantiation of the VF event. Such information may be displayed in real-time or stored, such as to determine response times, and to perform studies on effectiveness of rescuers as a function of the time since initiation of the event when a defibrillator is first connected and operable for the victim.

EXAMPLE

As for particular AMSA values for use in defining points 142 and 144, one example may be instructive. Data from an Utstein-compliant registry along with electronic ECG records were collected on consecutive adult non-traumatic OHCA patients treated by 2 EMS agencies over a 2 year period. Patients with bystander witnessed CA and with VF as initial CA rhythm were included (n=41). AMSA was calculated in earliest pause without compression artifacts, using a 2 second ECG with a Tukey (0.2) FFT window. VF duration was calculated as the sum of the time interval from collapse to defibrillator on and the time interval from defibrillator on to first CPR interruption for defibrillation delivery.

VF duration ranged between 6.5 and 29.6 min (11.3+4.1 min), with a corresponding AMSA between 2.1 and 16.4 mV-Hz (9.4+4.2 mV-Hz). AMSA measured in the circulatory phase (N=19) was significantly higher than that in the metabolic phase (N=22) (8.14+3.17 vs. 5.98+2.88, p=0.03). Linear regression revealed that AMSA decreased in the analyzed population by 0.22 mV-Hz for every min of VF. AMSA was able to predict circulatory phase with an accuracy of 0.7 in ROC area. An AMSA threshold of 10 mV-Hz was able to predict the circulatory phase with sensitivity of 32%, specificity of 95%, PPV of 86%, NPV of 62%, and overall accuracy of 66%.

Figure 2:
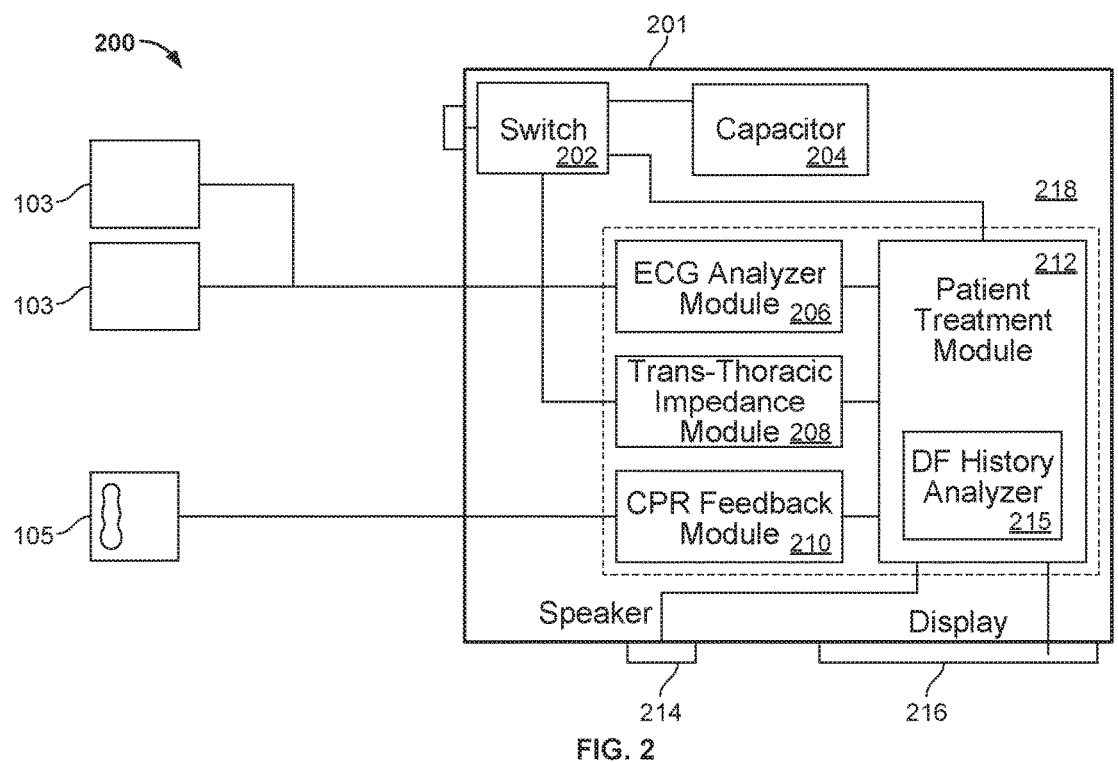
FIG. 2 is a block diagram that shows a defibrillator with an electrode package and compression puck.

Referring now to FIG. 2, a schematic block diagram 200 shows an example defibrillator 201, along with the example electrode package 103 and compression puck 105, of FIG. 1A in more detail. In general, the defibrillator 201, and optionally one or more of the electrode package 103 and compression puck 105, defines an apparatus for administering care to a patient, subject, or individual (e.g., patient 102) who requires cardiac assistance.

Figure 6:
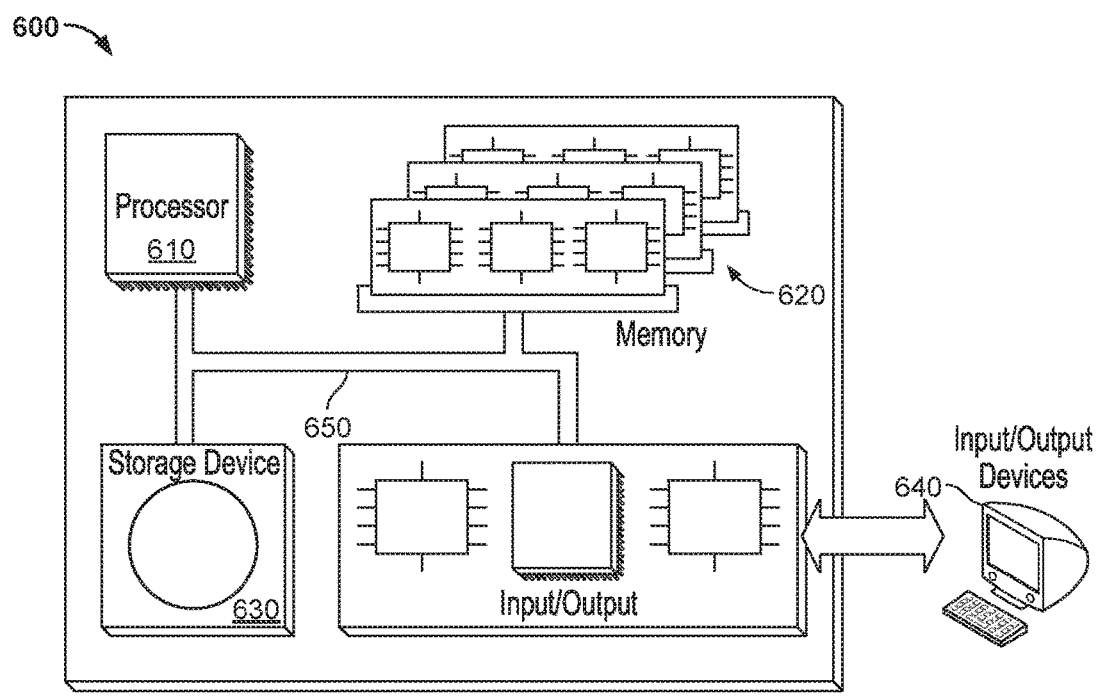
FIG. 6 shows a general computer system that can provide interactivity with a user of a medical device, such as feedback to a user in the performance of CPR.

The defibrillator 201 includes a switch 202 and at least one capacitor 204 for selectively supplying or applying a shock to a subject. The defibrillator 201 further includes an ECG analyzer module 206, a trans-thoracic impedance module 208, a CPR feedback module 210 that controls frequency and magnitude of chest compressions applied to a subject, a patient treatment (PT) module 212 (which includes a defibrillation history analyzer 215), a speaker 214, and a display 216. In this example, the ECG analyzer module 206, trans-thoracic impedance module 208, CPR feedback module 210, and patient treatment (PT) module 212 are grouped together as a logical module 218, which may be implemented by one or more computer processors. For example, respective elements of the logical module 218 can be implemented as: (i) a sequence of computer implemented instructions executing on at least one computer processor of the defibrillator 201; and (ii) interconnected logic or hardware modules within the defibrillator 201, as described in further detail below in connection with FIG. 6.

In the example of FIG. 2, the electrode package 103 is connected to the switch 202 via port on the defibrillator 201 so that different packages may be connected at different times. The electrode package 103 may also be connected through the port to ECG analyzer module 206, and trans-thoracic impedance module 208. The electrode package 103 includes electrodes for delivering a delivering a defibrillating electrical pulse to a patient in addition to capturing electrical signals from the heart that indicate ECG functioning. In this example there are a plurality of physical and signal (pairs of physical) leads so that vector representations of the ECG data may be collected and processed.

The compression puck 105 is connected, in this example, to the CPR feedback module 210. In one embodiment, the ECG analyzer module 206 is a component that receives an ECG signal. Similarly, the trans-thoracic impedance module 208 is a component that receives transthoracic impedance (e.g., trans-thoracic impedance signal 110). Other embodiments are also possible.

The patient treatment module 212 is configured to receive an input from each one of the ECG analyzer module 206, trans-thoracic impedance module 208, and CPR feedback module 210. The patient treatment module 212 uses inputs as received from at least the ECG analyzer module 206 and trans-thoracic impedance module 208 to predict whether a defibrillation event will likely terminate an arrhythmic episode. For example, ECG data can be used both to determine AMSA values for a patient (including via the vectorized methods described above and below), and also determine whether shocks are effective or not so that such information can be saved and used to identify likelihoods that subsequent shocks will be effective). In this manner, the patient treatment module 212 uses information derived from both an ECG signal (both for AMSA and for adjusting the AMSA value) and transthoracic impedance measurement to provide a determination of a likelihood of success for delivering a defibrillating shock to a subject.

The patient treatment module 212 is further configured to provide an input to each one of the speaker 214, display 216, and switch 202. In general, input provided to the speaker 214 and a display 216 corresponds to either a success indication or a failure indication regarding the likelihood of success for delivering a shock to the subject. In one embodiment, the difference between a success indication and a failure indication is binary and based on a threshold. For example, a success indication may be relayed to the display 216 when the chances corresponding to a successful defibrillation event is greater than 75%. In this example, the value "75%" may be rendered on the display 216 indicating a positive likelihood of success. When a positive likelihood of success is indicated, the patient treatment module 212 enables the switch 202 such that a shock may be delivered to a subject.

The patient treatment module 212 may also implement an ECG analyzer for generating an indication of heart rate for the patent, for generating an indication of heart rate variability for the patent, an indication of ECG amplitude for the patent, and/or an indication of a first or second derivative of ECG amplitude for the patient. The indication of ECG amplitude can include an RMS measurement, measured peak-to-peak, peak-to-trough, or an average of peak-to-peak or peak-to-trough over a specified interval. Such indications obtained by the ECG analyzer may be provided to compute an AMSA value for the patient and/or can be used in combination with a computed AMSA value so as to generate some derivative indication regarding whether a subsequent shock is likely or unlikely to be effective (and the degree, e.g., along a percentage scale, of the likelihood).

In another embodiment, likelihood of a successful defibrillation event may be classified into one of many possible groups such as, for example, low, medium, and high likelihood of success. With a "low" likelihood of success (e.g., corresponding to a successful defibrillation event is less than 50%), the patient treatment module 212 disables the switch 202 such that a shock cannot be delivered to a subject. With a "medium" likelihood of success (e.g., corresponding to a successful defibrillation event is greater than 50% but less than 75%), the patient treatment module 212 enables the switch 202 such that a shock may be delivered to a subject, but also renders a warning on the display 216 that the likelihood of success is questionable. With a "high" likelihood of success (e.g., corresponding to a successful defibrillation event is greater than or equal to 75%), the patient treatment module 212 enables the switch 202 such that a shock may be delivered to a subject, and also renders a cue on the display 216 indicating that the likelihood of success is very good. Still other embodiments are possible.

Thus, the system 200 may provide, in a portable electric device (e.g., a battery-operated device) the capability to analyze a number of inputs and to identify a variety of factors from those inputs, where the factors can then be combined to provide a flexible, intelligent determination of likely success.

Figure 3A:
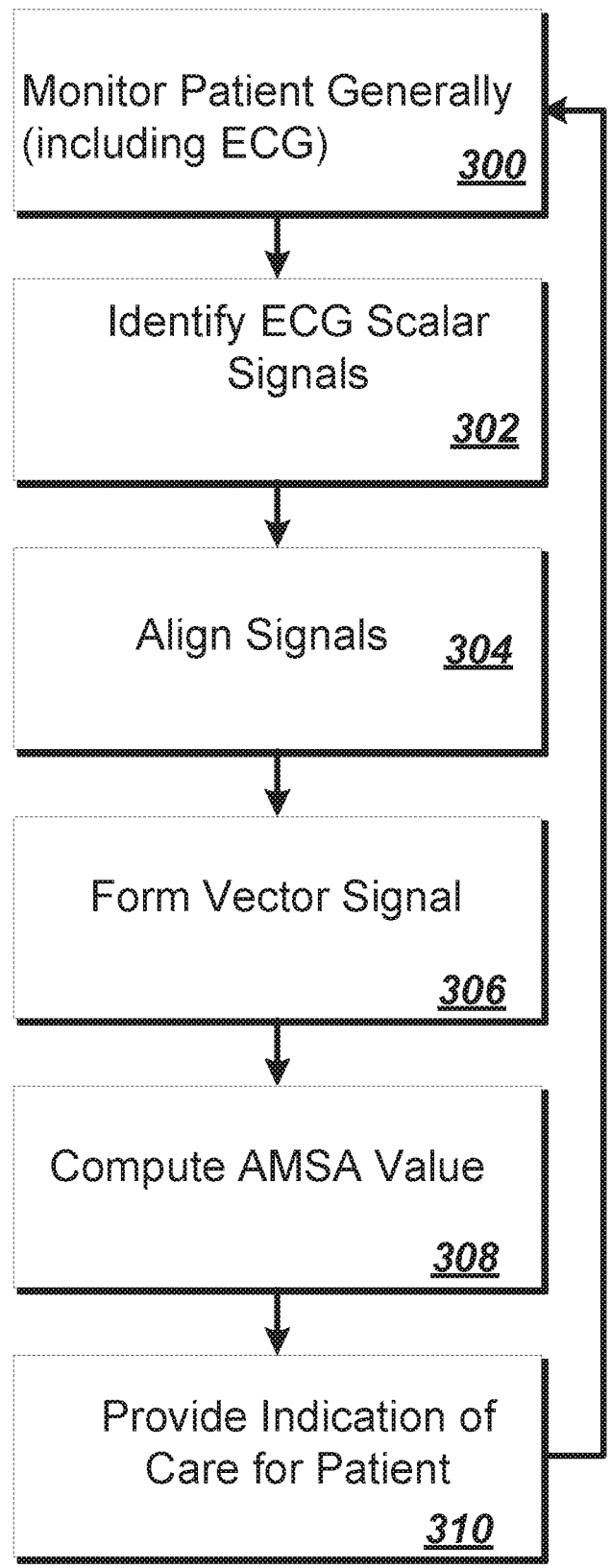
FIG. 3A is a flow chart of a process for providing a user with feedback regarding a likelihood that a defibrillating shock will be successful.

Referring now to FIG. 3A, there is shown a process for identifying a likelihood that a defibrillating shock will be effective, using vector input. The process begins at box 300, where a patient is generally monitored. The monitoring may take a familiar form and involve receiving signals from a plurality of different leads connected to a monitor that is part of a portable defibrillator. Other sensors can also be monitored, including an accelerometer in a CPR puck on the patient's chest, the patient's blood pressure and pulse, the patient's temperature, the patient's trans-thoracic impedance, and other relevant patient-related parameters.

At box 302, ECG scalar signals are identified from the sensed signals. In particular, signals from a plurality of leads (paired physical leads) can be captured using moving windows that scan across the incoming signals, and the signal may be digitized in a familiar manner for processing in certain implementations. The various scalar signals may be captured simultaneously for each of the leads and may be processed together.

At box 304, the signals are aligned so that they are orthogonal with each other. In particular, the locations of the electrodes on the patient may affect the relative phases of the different scalar signals. In this step, the scalar values may be adjusted so that they are orthogonal to each other or essentially orthogonal (e.g., where the lack of perfect orthogonality affects the predictive score by less than 5 or 10 percent).

At box 306, a vector signal is formed. Such a signal may be formed via the combination of two or more scalar values in a familiar manner, where the vector value has an amplitude and a direction, and where the direction may be envisioned as rotating through a cycle in a vector space with each beat of the patient's heart. The vector value represents a contribution from readings at multiple locations on the patient's torso, and thus is able to capture more aspects of the ECG signal.

At box 308, an AMSA value is computed using the vector signal. Such vectorized AMSA captures information from the multiple locations and indicates the amplitude of the spectrum area for those signals as combined into a vector value. The value returned may be in a typical AMSA form like those discussed above, or may be transformed into an equivalent value (and still be considered an AMSA value in that case).

At box 310, an indication of care for the patient is provided, where that indication is based at least in part on the computed AMSA value. In particular, the indication of care may include communicating to a rescuer whether a defibrillating shock for the patient is advised. Such communication may be made by indicating whether such a shock is currently enabled on a defibrillator and/or providing a value selected from multiple values along a scale where the selected value indicates a relative likelihood of success, such as by an A to F grade, or a percentage likelihood of success.

The indication of care may also be based on factors in addition to AMSA or another SPA indication. For example, the indication may additionally depend on the success or failure of prior shocks, the amount of time the patient has been undergoing cardiac arrest, determinations of pharmaceuticals that have been administered to the patient, the patient's age and weight and gender, and other variables that have been determined to be relevant to the likelihood calculation. The particular signals used in determining the likelihood, and the way it is presented to a rescuer, may vary depending on whether the rescuer is lay or expert (e.g., as determined by whether the defibrillator is operating as an AED or a professional defibrillator), such as by taking into account more factors and providing more information to professional rescuers.

Figure 3B:
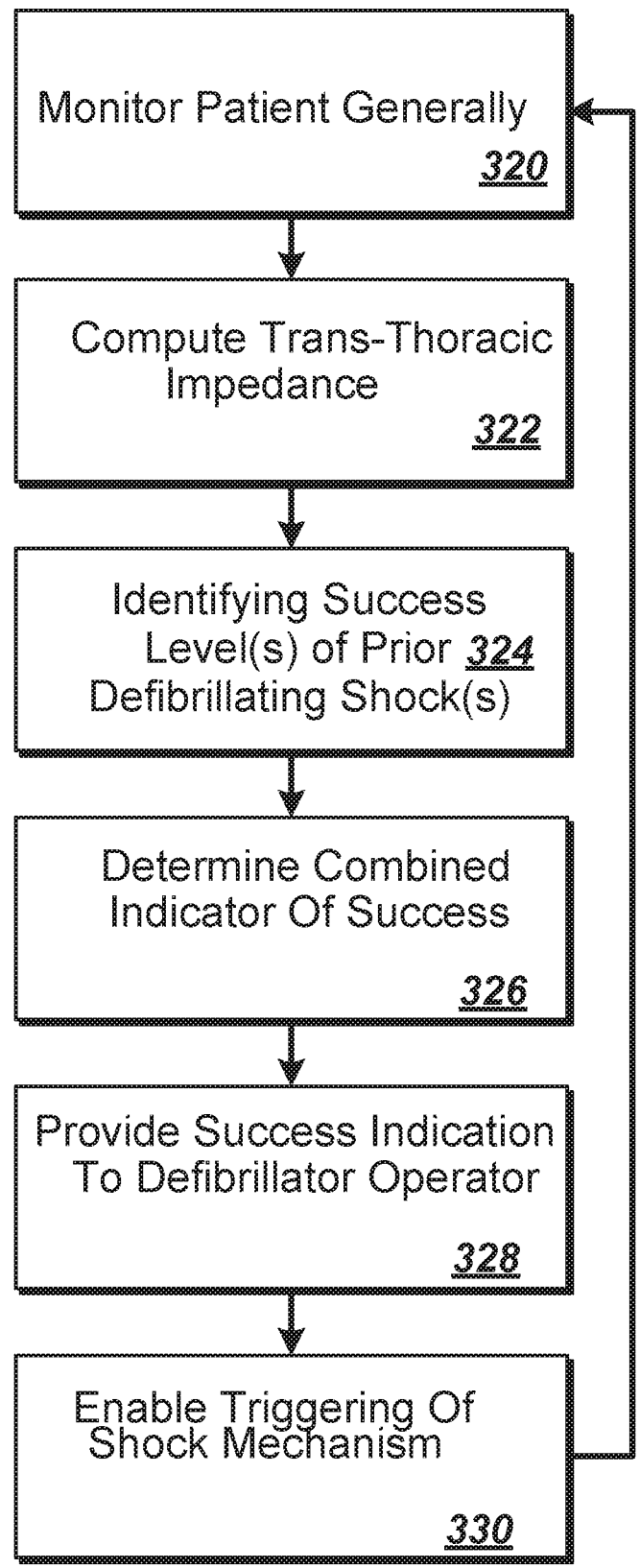
FIG. 3B is a flow chart of a process for identifying a phase in a cardiac event so as to provide guidance to a rescuer.
Figure 3C:
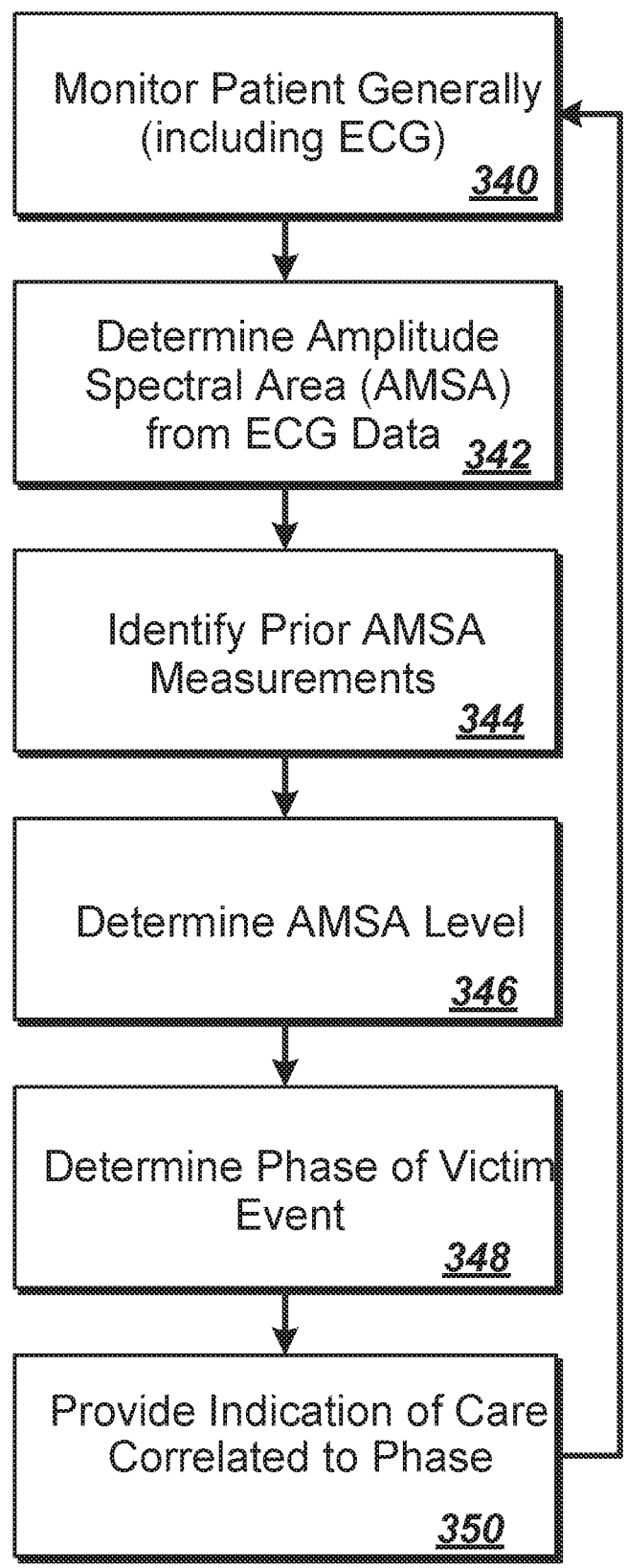
FIG. 3C is a flow chart of a process for using ECG vectors to determine likelihood of success for defibrillating a patient.

FIG. 3B shows an example method for administering care to an individual requiring cardiac assistance. In one embodiment, the method is implemented by the example defibrillators described above in connection with FIGS. 1A-D and 2.

However, other embodiments are possible. The method is similar to that described for FIG. 3A, but focuses less on the processing of vector inputs, and more on the combining of various different signals for computing a likelihood of success for a defibrillating shock.

At box 320, at least one of an ECG signal and a trans-thoracic impedance signal (e.g., trans-thoracic impedance signal 110) of the subject receiving cardiac care is monitored. In general, an individual receiving cardiac care includes the individual at any time during a cardiac event, including whether or not individual is receiving active care (e.g., chest compressions). The ECG signal may be scalar in character or a vector form that is a combination of multiple scalar signals.

At box 322, a trans-thoracic impedance value is extracted from the trans-thoracic impedance signal as monitored at step 320. Additionally, at step 322, an AMSA value can be calculated from the ECG signal as monitored at step 320 by integrating the Fourier transform (e.g., FFT) of the ECG signal over a finite frequency range. Example frequency content of an arrhythmic ECG signal generally ranges between about 1 Hz to about 40 Hz, with amplitude of about 50 mV or less. An example of an AMSA value calculated from such a signal ranges between about 5 mV-Hz to about 20 mV-Hz. Also, values that are transformable to AMSA values of the form just given are considered to be AMSA values also for purposes of this document. It will be appreciated however that this is only an example, and that the magnitude and spectra of an ECG signal ranges greatly.

The AMSA value may be determined from a moving window (or moving windows for each scalar value that makes up a vector) that moves in time through the incoming ECG data as it arrives (e.g., the raw ECG data may be cached for a period at least as long as the window), where the window may be about one second wide (or more), and can be measured multiple times each second so that there are overlapping windows. The window may also have a tapered (rather than rectangular) window function so as to improve the accuracy of the AMSA value in predicting defibrillation success. Furthermore, the coefficients for the window may be selected to maximize the predictive ability of the system. In addition, multiple different AMSA values may be determined (e.g., with different window size, type, and/or coefficients) and a most-accurate AMSA may be determined and used to make a prediction, or a composite value may be generated from each of the determined AMSA values.

Additionally, the window size, type, and coefficients can change over time to allow a system to dynamically adjust to a particular VF event. For example, using determinations about the phase in which a VF event is, a system may change such parameters to switch to a window that is determined to better predict defibrillation success. Alternatively, a blend of window techniques may be used and the blend may change over time, while a composite prediction score is determined from the blended techniques.

At box 324, the process identifies success levels of prior shocks applied to the patient during the cardiac event. Such determination may occur in various manners. At a simplest level, the process may simply track the number of times a defibrillating shock has been provided to the patient. In more complex implementations, the process may identify how many attempts were successful and how many were not, and in a slightly more complex implementation, may identify which were successful and which were not (e.g., because subsequent steps may perform more accurately by weighting the influence of different ones of the prior defibrillations in different ways). In yet more complex systems, the degrees of prior success can be determined, which may include determining how close the patient's defibrillated heart rate was to a predetermined rate (either a particular rate or a range of rates) or how consistent the rate was over time, or a combination of both to generate a score for the quality of the defibrillation. Other examples of physiologic measure that may be useful for generating a score may be pulse oximetry, capnography, blood pressure, or other pulse or blood flow detection methods.

As one such example, scoring the ECG quality of the post-shock ECG rhythm may occur by giving heart rates in the range of 50-90 BPM a higher score than those above or below that range (with the score decreasing the further from that range the heart rates were). More complex scoring systems could additionally or alternatively be used, such as using a windowing function that weights a heart rate of a patient to generate a normalized score. Such a windowing functions might be a Hamming window or a Tukey window with a rectangle width that is flat from 50-90 BPM. In each such situation, the data gathered for each defibrillation may be saved so that it can be accessed in preparation for determining and providing identifications of likely success for later defibrillations.

At box 326, the process determines a combined indicator of success that includes an indication from trans-thoracic impedance and an indication from an ECG reading, such as an AMSA indication, and is modified appropriately to reflect data about prior successes or failure in defibrillation. The combined indicator may be determined by inputting a trans-thoracic impedance value, an AMSA value, and a count or other indicator of prior success or failure, into a function or look-up table, or may be determined without a need to compute both or all values first, such as by taking inputs indicative of all values and computing a predictor of success directly from such indicative values. Alternatively to using a table to calculate the predictive score, the use of logistic regression may be used with a logistic regression equation, with inputs to the equation with, e.g. ECG rhythm type, ECG rate, transthoracic impedance, prior shocks, etc. Neural network or fuzzy logic methods or other non-linear decision-making methods may also be used. In certain instances, a single value, like AMSA may be used to compute the likelihood of success.

At box 328, a success indication is provided to a defibrillator operator. The indication may take a variety of forms. For example, the ability of the defibrillator to deliver a shock may be enabled when the indicator of success is higher than a threshold level, so that the success indicator is delivered by the operator being shown that a shock can or cannot be delivered. Also, the operator may be notified that the defibrillator can provide a shock, and may be prompted to push a physical button to cause the shock to be delivered.

In some implementations, the operator may also be provided with more detail about the success indication. For example, the operator may be shown a percentage number that indicates a likelihood in percent that the shock will be successful. Alternatively, or in addition, the operator may be shown a less granular level of an indication, such as a value of "excellent," "good," and "poor" to indicate to the operator what the likelihood of successful defibrillation is.

At box 330, the trigger mechanism is enabled on the defibrillator, as discussed above. In certain instances, such a feature may be enabled whenever a shockable rhythm is observed for a patient. In other circumstances, the enabling may occur only when the combined indication discussed above exceeds a threshold value for indicating that a shock will be successful in defibrillating the patient. For a hybrid defibrillator that is capable of manual and AED modes, the trigger mechanism may operate different depending on what mode the defibrillator is in.

An arrow is shown returning to the top of the process to indicate that the process here is in ways continuous and in ways repeated. In particular, ECG signals are gathered continuously, as are other types of data. And the process repeatedly tries to identify whether a shock can or should be provided, and the order and timing of the steps in that cycling may be dictated by standards as adjusted by a medical director or other appropriate individual responsible for the deployed defibrillator. Thus, for instance, the entire process may be repeated, certain portions may be repeated more frequently than others, and certain portions may be performed once, while others are repeated.

FIG. 3B is a flow chart of a process for identifying a phase in a cardiac event so as to provide guidance to a rescuer. In general, the process involves using AMSA or other determinations to identify a length of time since a cardiac event has begun and/or a phase in which the event is currently located, where different phases are delineated by the relative likelihood of certain treatment approaches operating successfully vis-à-vis other phases.

The process in this example begins at box 340, where a patient is monitored generally, such as by monitoring the patient's pulse and ECG, among other things. Such monitoring may be the same monitoring as in step 320 in FIG. 3B or may occur concurrently with such monitoring. The monitoring may constitute constantly receiving ECG data and periodically computing (e.g., every second or every two seconds) AMSA and other values from it. At the same time, an ECG representation may be displayed to an operator of a defibrillator or other medical device.

At box 342, the AMSA is determined, and may be calculated in known manners from the ECG data. Other SPAs may also be operated on the incoming data from the patient. As discussed above, the AMSA value may depend on a window function of a certain determined length and type, and having certain determined coefficients, where each of these parameters may be adjusted dynamically over the time of a VF incident.

At box 344, prior AMSA measurements are identified. Such a step may occur simply by looking to a known location in memory where a software program has been programmed to store such information. Those measurements or computations may be loaded to a location at which they can be manipulated relative to each other, including by combining those separate measurements into a composite, such as an average of the measurements. In obtaining such measurements, the process may fetch only n number of prior measurements with each cycle of the process, so that a rolling or sliding average is computed at each step. The number of values to combine in any given cycle can be selected so as to provide sufficient responsiveness (fewer readings) while providing a sufficient general view of the status of the patient that is not subject to extreme fluctuations (more readings).

At box 346, the current general AMSA level (e.g., from an average of multiple prior readings) is determined. Other measures of a similar type may also or alternatively be generated, if they represent the progression of the patient through nonrecurring phases of a cardiac event, such as those discussed above.

At box 348, the phase in the progression of the VF event is determined for the patient. Such a determination may include simply estimating, with the AMSA level or other such data, the time since the patient entered cardiac arrest, and/or more generally whether the patient is in electrical, circulatory, or metabolic phase. For example, the AMSA level for the patient may be provided to a look-up table that maps observed AMSA values for a population to event phases or time since the event started, or both.

At box 350, the process provides an indication of care that is correlated to the phase of the event. For example, a screen on a defibrillator may show a message indicating that the rescuer should prepare to administer a shock (e.g., if the patient is in electrical phase and the AMSA determination shows a high likelihood that the shock will be successful). Similarly, color may be used to show one or more of the parameters, such as a single color bar to show likelihood of shock success, where the likelihood is based on current AMSA, combined AMSA values (e.g., an average or trend), or a combination of both.

Figure 4A:
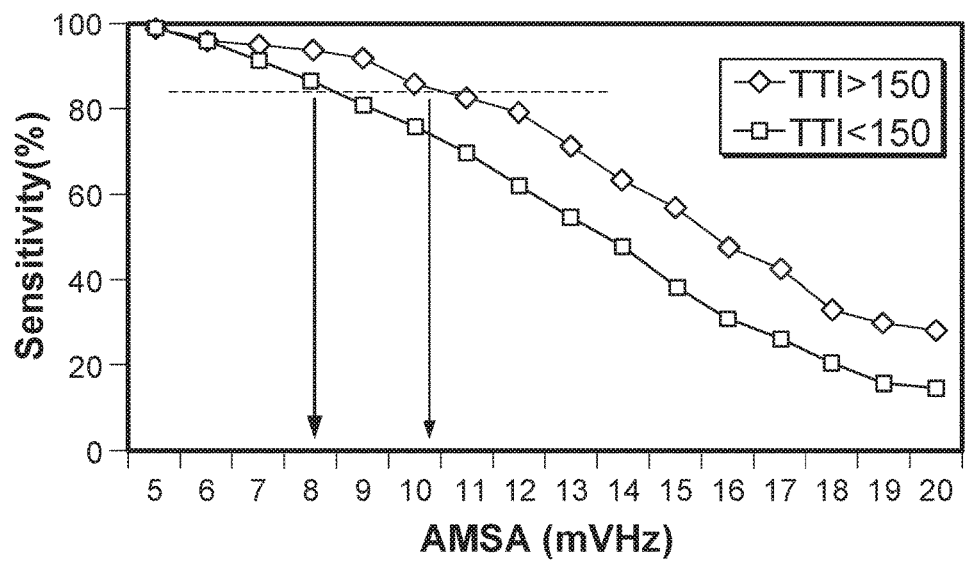
FIGS. 4A and 4B are graphs showing relationships between sensitivity and specificity, and AMSA threshold values for groups of patients.

FIG. 4A shows a plot of sensitivity (%) versus AMSA threshold (mv-Hz) for a first set of subjects having a trans-thoracic impedance (TTI) measured greater than 150 ohms, and a second set of subjects having a trans-thoracic impedance measured less than 150 ohms. The data shows the influence of TTI on the prediction accuracy of AMSA for shock success at different threshold values as presented in sensitivity and specificity.

The data was obtained by collecting data from defibrillators used in real rescue events from multiple emergency medical services in the United States through regular field case submission to ZOLL Medical Corporation, and where individual personal identifying information could not be determined from the gathered data. All reporting parties used ZOLL automatic external defibrillators that included current-based impedance compensation. The sampling rate for ECG data was 250 Hz, and analysis was performed on a selection of an episode of 2.05 seconds (512 data points) ending at 0.5 seconds before each shock attempt. Shock success was defined as an organized rhythm for a minimum of 30 seconds, starting 60 seconds after the delivered shock, and with a rate of 40 beats per minute or greater. A total of 1292 shocks (305 successful) form 580 patients with VF were included in the analysis. AMSA. The TTI was measure at shocking pads placed on each respective subject.

As shown by the comparative data, a patient's TTI affects the predictability of AMSA by shifting the threshold upward for a given sensitivity or specificity value. AMSA value was significantly higher when the TTI was greater than 150 ohm (11.6±8.9 vs. 9.8±7.1, p=0.002) as compared with those shocks with TTI less than 150 ohm. The AMSA threshold value was increased from 8.2 mvHz to 10.3 mvHz when sensitivity was set to 85%. Such information can be used to provide a real-time adjustment mechanism, like those discussed above, that adjusts an AMSA threshold for predicting likelihood of shock success or otherwise taking into account the real-time measured TTI so as to affect the reported likelihood in a manner that makes it more accurate.

Figure 4B:
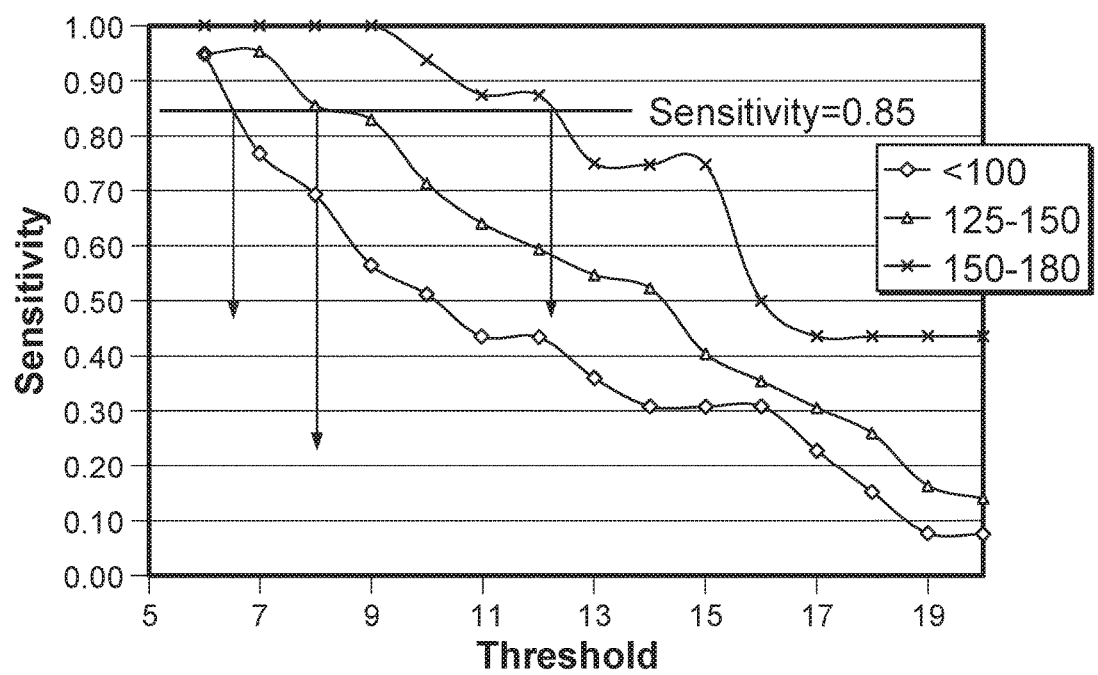

FIG. 4B shows a plot of specificity (%) versus AMSA threshold (mv-Hz) for a first set of subjects having a trans-thoracic impedance measured less than 150 ohms, a second set of subjects having a trans-thoracic impedance greater than 150 ohms. The tested subjects and data collection were the same as for the graph in FIG. 4A. As shown by the comparative data, AMSA threshold generally increases, for a given specificity, with increasing trans-thoracic impedance. For example specificity at a threshold of 85% was 11.8 mvHz for TTI<150 ohms, and 14.2 mvHz for TTI>150 ohms. Again, analysis of such data may be used in programming devices to provide predictions of likelihood of shock success, or to disable or enable the ability to shock a particular patient, based on calculated AMSA values.

Figure 5:
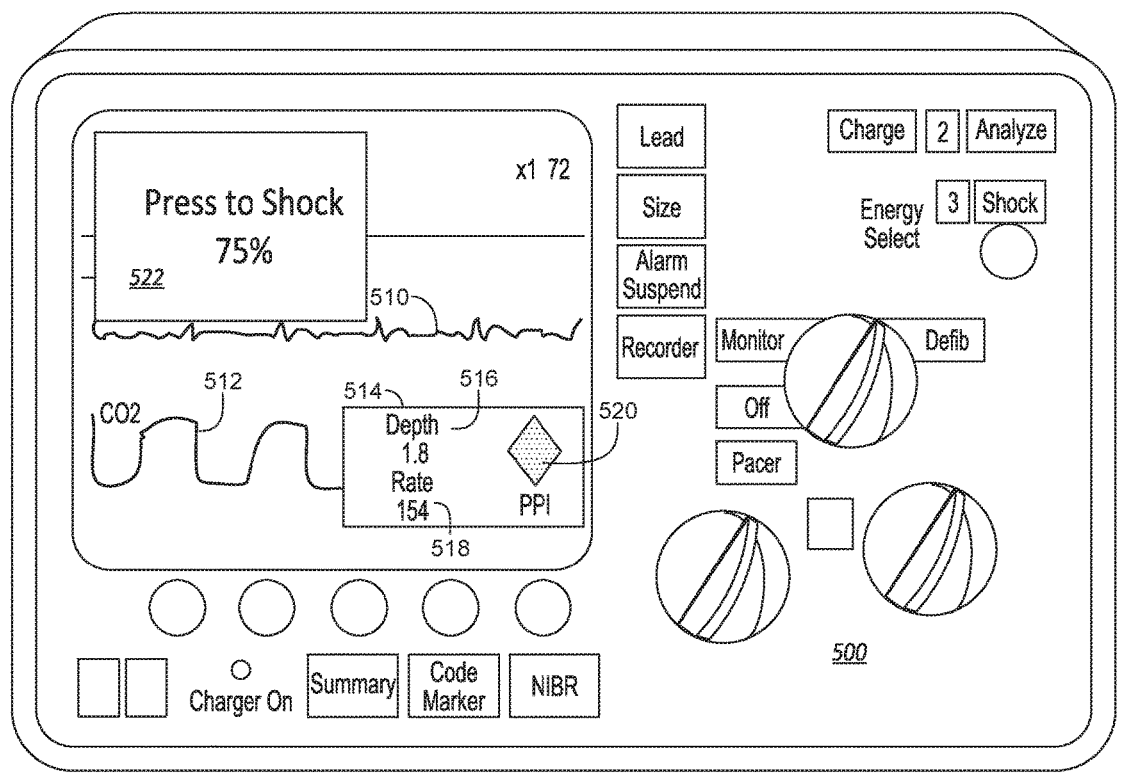
FIG. 5 illustrates a defibrillator showing certain types of information that can be displayed to a rescuer.

FIG. 5 shows a defibrillator showing certain types of information that can be displayed to a rescuer. In the figure, a defibrillation device 500 with a display portion 502 provides information about patient status and CPR administration quality during the use of the defibrillator device. As shown on display 502, during the administration of chest compressions, the device 500 displays information about the chest compressions in box on the same display as is displayed a filtered ECG waveform and a CO2 waveform (alternatively, an SpO2 waveform can be displayed).

During chest compressions, the ECG waveform is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled Method and Apparatus for Enhancement of Chest Compressions During Chest Compressions, the contents of which are hereby incorporated by reference in its entirety.

Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions.

The CPR information in box 514 is automatically displayed when compressions are detected by a defibrillator. The information about the chest compressions that is displayed in box 514 includes rate 518 (e.g., number of compressions per minute) and depth 516 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

The information about the chest compressions that is displayed in box 514 also includes a perfusion performance indicator (PPI) 520. The PPI 520 is a shape (e.g., a diamond) with the amount of fill that is in the shape differing over time to provide feedback about both the rate and depth of the compressions. When CPR is being performed adequately, for example, at a rate of about 101 compressions per minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

As shown in display 502, the filtered ECG waveform 510 is a full-length waveform that fills the entire span of the display device, while the second waveform (e.g., the CO2 waveform 512) is a partial-length waveform and fills only a portion of the display. A portion of the display beside the second waveform provides the CPR information in box 514. For example, the display splits the horizontal area for the second waveform in half, displaying waveform 512 on left, and CPR information on the right in box 514.

The data displayed to the rescuer can change based on the actions of the rescuer. For example, the data displayed can change based on whether the rescuer is currently administering CPR chest compressions to the patient. Additionally, the ECG data displayed to the user can change based on the detection of CPR chest compressions. For example, an adaptive filter can automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

Also shown on the display is a reminder 521 regarding "release" in performing chest compression. Specifically, a fatigued rescuer may begin leaning forward on the chest of a victim and not release pressure on the sternum of the victim at the top of each compression. This can reduce the perfusion and circulation accomplished by the chest compressions. The reminder 521 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication may be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback.

Moreover, there is shown in box 522 an indication of a likelihood that a shock, if currently administered, will be effective in defibrillating the patient. Here, the likelihood is indicated as being 75%, which is above a threshold value, so the defibrillator 500 is recommending that the rescuer press a button that will operate a switch to cause energy to be discharged into the patient. The likelihood determination may have been made by a process that takes in vector ECG values, and produces an AMSA value (repeatedly) for the patients using such data as it arrives on a plurality of leads that are connected to the patient via electrodes and to the defibrillator 500 wire one or more ports into which the physical ECG leads can be plugged in a familiar manner.

The particular displays shown in FIG. 5 may be implemented, as noted above, with a system that uses particular techniques to improve the accuracy of a prediction that an applied shock will be a success and that uses AMSA or other SPA values in making such a prediction. For instance, the feedback provided by the displays in the figures can be determined by selecting an appropriate ECG window size for calculating AMSA on vectorized values (e.g., one second or slightly longer, such as 1.5 seconds or 2 seconds), a window type (e.g., Tukey), and particular coefficients for the window. Such factors can also be changed over the time of a VF event, as discussed above, so as to maintain a most accurate predictor of defibrillation success.

While at least some of the embodiments described above describe techniques and displays used during manual human-delivered chest compressions, similar techniques and displays can be used with automated chest compression devices such as the AUTOPULSE device manufactured by ZOLL Medical Corporation of Chelmsford, Mass.

The particular techniques described here may be assisted by the use of a computer-implemented medical device, such as a defibrillator that includes computing capability. The computing portions of such defibrillator or other device is shown generally in FIG. 6, and may communicate with and/or incorporate a computer system 600 in performing the operations discussed above, including operations for computing the quality of one or more components of CPR provided to a victim and generating feedback to rescuers, including feedback to change rescuers who are performing certain components of the CPR. The system 600 may be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. A defibrillation system for managing care of a person, the defibrillation system comprising:
    an external defibrillator having one or more capacitors arranged to deliver a defibrillating shock to the person receiving emergency cardiac assistance;
    a plurality of electrodes configured to be coupled to the person and acquire a plurality of electrocardiogram (ECG) signals from the heart of the person; and
    a patient treatment module executable on one or more computer processors using code stored in non-transitory media and configured to execute operations comprising:
        receiving the plurality of ECG signals acquired by the plurality of electrodes,
        determining an ECG vector representation of the plurality of ECG signals comprising at least two orthogonal or near orthogonal signals indicative of an ECG electrical vector of the person, wherein the ECG vector representation includes information of both magnitude and direction of the ECG electrical vector,
        identifying an angle of the ECG vector representation to provide an indication of whether the defibrillating shock should be delivered to the person via the one or more capacitors, and
        delivering the defibrillating shock to the person based on the identified angle of the ECG vector representation.

2. The system of claim 1, wherein the operations comprise performing on the plurality of ECG signals at least one of one or more Fast Fourier Transforms (FFTs) and one or more amplitude spectrum area calculations.

3. The system of claim 1, wherein the operations comprise applying a pre-transform to the plurality of ECG signals so as to decrease an error of determining a likelihood of success from delivering the defibrillating shock to less than about 10 percent.

4. The system of claim 3, wherein the pre-transform is applied in response to determining that the plurality of ECG signals were not previously orthogonal or near orthogonal.

5. The system of claim 3, wherein the patient treatment module is programmed to apply a mathematical computation to the vector representation by calculating FFT for each of the plurality of ECG signals to create processed values and then combining the processed values.

6. The system of claim 5, wherein combining the processed values comprises determining a root of a sum of the processed values.

7. The system of claim 1, wherein the operations comprise performing a mathematical transform on the plurality of ECG signals from a time domain to a frequency domain on a window of data.

8. The system of claim 7, wherein the window comprises a tapered window.

9. The system of claim 8, wherein the tapered window is between about one second and about 2 seconds in width.

10. The system of claim 8, wherein the tapered window is selected from a group consisting of Tukey, Hann, Blackman-Harris, and Flat Top.

11. The system of claim 1, wherein the indication comprises a likelihood of success from delivering the defibrillating shock with the one or more capacitors to the person.

12. The system of claim 1, wherein the system is programmed to display to a user one of multiple possible indications that each indicates a degree of likelihood of success from delivering the defibrillating shock.

13. The system of claim 12, where the patient treatment module is programmed to determine whether a prior defibrillation shock was at least partially successful, and based at least in part on the determination of whether the prior defibrillation was at least partially successful, modifying a calculation of the likelihood of success from delivering the defibrillating shock.

14. The system of claim 12, wherein the indication of the likelihood of success from delivering the defibrillating shock to the person depends on a determination of whether one or more prior shocks delivered to the person were successful in defibrillating the person.

15. The system of claim 1, wherein the operations comprise performing a mathematical computation on the plurality of ECG signals, the mathematical computation comprising a transform selected from a group consisting of Fourier, discrete Fourier, Hilbert, discrete Hilbert, wavelet, and discrete wavelet methods.

16. The system of claim 1, wherein the patient treatment module is programmed to determine a likelihood of success from delivering the defibrillating shock using at least one patient-dependent physical parameter separate from a patient ECG reading.

17. The system of claim 16, wherein the patient treatment module is programmed to determine the likelihood of success from delivering the defibrillating shock using a measure of trans-thoracic impedance of the person.

18. A method for managing care of a person, the method comprising:
monitoring, with an external defibrillator, electrocardiogram (ECG) data from the person receiving emergency cardiac assistance, the ECG data defining an ECG vector representation from a plurality of ECG signals;
performing a vectorized mathematical transform of the ECG data that defines the ECG vector representation from a time domain to a frequency domain using a window in the time domain;
identifying an angle of the ECG vector representation to provide an indication of whether a defibrillating shock should be delivered to the person via one or more capacitors; and
delivering the defibrillating shock to the person based on the identified angle of the ECG vector representation.

19. The method of claim 18, wherein the vectorized mathematical transform comprises at least one of one or more vectorized Fast Fourier Transforms (FFTs) and one or more amplitude spectrum area (AMSA) calculations.

20. The method of claim 18, further comprising applying a pre-transform to the plurality of ECG signals before applying the vectorized mathematical transform so as to make the plurality of ECG signals orthogonal or near orthogonal.

21. The method of claim 18, further comprising applying the mathematical transform to a vector value by calculating FFT for each of the plurality of ECG signals to create processed values, and then combining the processed values.

22. The method of claim 18, wherein the mathematical transform comprises a transform from the time domain to the frequency domain on a window of ECG data.

23. The method of claim 22, wherein the window comprises a tapered window.

24. The method of claim 23, wherein the tapered window is between about one second and about two seconds wide.

25. The method of claim 23, wherein the tapered window is selected from a group consisting of Tukey, Hann, Blackman-Harris, and Flat Top.

26. The method of claim 18, further comprising determining a likelihood of future defibrillation shock success based on the vectorized mathematical transform.

27. The method of claim 26, wherein determining the likelihood of future defibrillation shock success comprises at least one of determining an amplitude spectrum area (AMSA) value for the ECG data and determining a value that is a function of electrocardiogram amplitude at particular different frequencies or frequency ranges.

28. The method of claim 27, wherein determining the likelihood of future defibrillation shock success further comprises adjusting the determined AMSA value using information about a prior defibrillation shock, and performing a calculation by an operation selected form a group consisting of logistic regression, table look-up, neural network, and fuzzy logic.

29. The method of claim 28, further comprising determining whether the adjusted AMSA value exceeds a predetermined threshold value.

30. The method of claim 29, further comprising providing to a rescuer a visual, audible, or tactile alert that a shockable situation exists for the person receiving emergency cardiac assistance.

31. The method of claim 18, further comprising determining whether a prior defibrillation shock was at least partially successful, and based at least in part on the determination of whether the prior defibrillation was at least partially successful, modifying a calculation of a likelihood of success from delivering the defibrillating shock.

32. The method of claim 18, where the indication of whether the defibrillating shock should be delivered to the person is determined using at least one patient-dependent physical parameter separate from a patient ECG reading.

33. The method of claim 32, wherein the at least one patient-dependent physical parameter comprises an indication of trans-thoracic impedance of the person receiving emergency cardiac assistance.

34. The method of claim 33, wherein the indication of trans-thoracic impedance is determined from signals sensed by a plurality of electrocardiogram leads that also provide the ECG data.

35. The method of claim 18, further comprising identifying compression depth of chest compressions performed on the person receiving emergency cardiac assistance, using a device on the person's sternum and in communication with the external defibrillator, and providing feedback to a rescuer performing the chest compressions, the feedback regarding rate of compression, depth of compression, or both.

* * * * *